US008361412B2

(12) United States Patent
Yasuda et al.

(10) Patent No.: US 8,361,412 B2
(45) Date of Patent: Jan. 29, 2013

(54) CELL MEASURING AND SORTING CHIP

(75) Inventors: Kenji Yasuda, Tokyo (JP); Akihiro Hattori, Tokyo (JP); Kazunori Okano, Tokyo (JP)

(73) Assignees: Japan Science and Technology Agency, Saitama (JP); Onchip Biotechnologies, Inc., Tokyo (JP)

( * ) Notice: Subject to any disclaimer, the term of this patent is extended or adjusted under 35 U.S.C. 154(b) by 1090 days.

(21) Appl. No.: 11/317,004

(22) Filed: Dec. 27, 2005

(65) Prior Publication Data

US 2006/0194307 A1 Aug. 31, 2006

(30) Foreign Application Priority Data

Dec. 28, 2004 (JP) ................................ 2004-379327

(51) Int. Cl.
*B01L 3/00* (2006.01)
(52) U.S. Cl. .......... 422/502; 422/503; 436/63; 436/164; 436/172
(58) Field of Classification Search .................. 422/502, 422/503; 436/52, 164, 172
See application file for complete search history.

(56) References Cited

U.S. PATENT DOCUMENTS

| 5,372,946 A | * | 12/1994 | Cusak et al. | 436/69 |
| 5,405,366 A | * | 4/1995 | Fox et al. | 607/50 |
| 5,611,339 A | * | 3/1997 | Okabe et al. | 600/372 |
| 6,149,870 A | * | 11/2000 | Parce et al. | 422/100 |
| 7,214,298 B2 | * | 5/2007 | Spence et al. | 204/450 |
| 2002/0192113 A1 | * | 12/2002 | Uffenheimer et al. | 422/67 |
| 2006/0141618 A1 | * | 6/2006 | Yasuda et al. | 435/325 |

FOREIGN PATENT DOCUMENTS

| JP | 2002-503334 | 1/2002 |
| JP | 2003-107099 | 4/2003 |
| JP | 2004-85323 | 3/2004 |
| WO | WO 98/10267 | 3/1998 |
| WO | WO 2004/101731 A1 | 11/2004 |

OTHER PUBLICATIONS

Michael E. Kamarck, "Fluorescence-Activated Cell Sorting of Hybrid and Transfected Cells", Methods Enzymol, vol. 151, p. 150-165 (1987).
Micro Total Analysis, pp. 77-80 (Kluwer Academic Publishers, 1998); Analytical Chemistry, 70, pp. 1909-1915.

* cited by examiner

*Primary Examiner* — Krishnan S Menon
*Assistant Examiner* — Dwan A Gerido
(74) *Attorney, Agent, or Firm* — Antonelli, Terry, Stout & Kraus, LLP.

(57) ABSTRACT

A cell sorting device using an inexpensive chip capable of being exchanged for each sample. The chip includes: a first flow path allowing buffer fluid containing cells to flow down; second and third flow paths which put the first flow path therebetween and allow buffer fluid not containing cells to flow down; a fourth flow path which allows the buffer fluid as a single flow path formed by joining the buffer fluids in the other three flow paths; a cell detecting region for detecting cells flowing with the buffer fluid down the fourth flow path; and a cell sorting region for sorting the cells according to a type of the cells detected. The first to fourth flow paths are cascaded, are supplied with the buffer fluid from reservoirs with the same fluid level, and have substantially the same width or cross-section area.

7 Claims, 13 Drawing Sheets

CELL MEASURING AND SORTING CHIP

FIELD OF THE INVENTION

The present invention relates to a cell sorter.

BACKGROUND OF THE INVENTION

An anatomy of a multicellular organism retains a harmonious function as a whole by each cell taking a separate role. Otherwise, when part of the cells becomes cancerous (hereinafter referred to as a cancer, including tumors), the part grows into a neoplasm different from its peripheral region. However, the cancerous region and a normal tissue region away therefrom may not necessarily be sorted by a certain borderline, that is, the region surrounding the cancer is affected in some way. In order to analyze a function of an organ tissue, therefore, it is necessary to sort a small number of cells present in a small region.

Otherwise, in the medical field, in order to examine a region suspected of a cancer in the normal tissue, it is necessary to sort the region suspected of the cancer from a piece of tissue sorted in biopsy. For separation of such specific cells, it is common to fix the cells, perform various cell staining, and cut out a target part. A method called laser microdissection has been recently developed for correcting target cells only in a region subjected to the laser.

Otherwise, in the field of regeneration medicine, there is an endeavor to sort a stem cell from the tissue, cultivate the stem cell, and conduct the differentiation induction to regenerate the target tissue, and furthermore an organ.

To classify, identify or sort cells, it is necessary to distinguish the different cells according to a certain reference. Common methods of distinguishing cells include the following:

1) Visual cell classification based on morphology: an examination for a bladder cancer, an urethral cancer and the like by detection of an atypical cell present in urine, and a cancer screening by a classification of the atypical cells in blood or a cytological diagnosis in the tissue can be taken as examples.

2) Cell classification based on the cell surface antigen (marker) staining by the fluorescent antibody test: this is to stain a cell surface antigen, generally called as a CD marker, with a fluorescent labeling antibody specific thereto, and used for cancer screenings by a cell sorting using a cell sorter, a flow cytometer, or tissue staining. These techniques are frequently used not only in the medical field but also for the cytophysiological study and the industrial use of the cells.

3) Separation of a stem cell involves an example of purifying a differentiated target stem cell from roughly separated stem cells using a fluorescent pigment taken into a cell as a reporter and by actually re-cultivating the differentiated stem cell afterward. That is to say, since an effective marker for the stem cell has not yet been established, the target cell is selected by their differentiated characteristics of cells after their cultivation.

Separating and retrieving a specific cell in a culture fluid in this way is an important technique for biological and medical analyses. When cells are sorted based on a difference in the specific gravity of the cells, the cells can be sorted by the velocity sedimentation method. However, when there is little difference in the specific gravity of the cells enough to differentiate a non-sensitized cell from a sensitized cell, it is necessary to sort the cells one by one based on information from staining with the fluorescent antibody or other visual information. This technique may be represented by, for instance, a cell sorter. The cell sorter employs the technique as follows: The cells after the fluorescent staining processing are dropped into a charged droplet as isolated in the unit of cell, and a high electric field is irradiated in any direction on the plane perpendicular to the dropping direction in the process of the droplet dropping, whereby the dropping direction of the droplet is controlled by the irradiated voltage, based on the optical measurement of the presence and localization of the fluorescence in the cell in the droplet and the intensity of the light scattering diffraction, to fractionate and retrieve the droplet in a plurality of containers placed at the bottom (non-patent document 1: Kamarck, M. E., Methods Enzymol. Vol. 151, p 150-165 (1987)).

However, this technique involves the following problems: the cost is high; the system is large; a high electric field of some thousand volts is required; a large amount of samples is required; cells may be damaged during generation of the droplets; the sample cannot be directly observed. To solve these problems, a cell sorter has been recently developed which generates fine flow paths using the micromachining technology and sorts the cells flowing through the laminar flow in the flow path while directly observing them under a microscope (non-patent document 2: Micro Total Analysis, 98, pp. 77-80 (Kluwer Academic Publishers, 1998); Analytical Chemistry, 70, pp. 1909-1915 (1998)). However, since the cell sorter which generates the fine flow paths using the microfabrication technology is slow in the response speed of the sample sorting with respect to the observation unit, another processing method that does not damage the sample and is faster in response is required in order to put the cell sorter into practical use.

In order to solve the problems, the present inventors have filed the applications for a cell analyzer/sorter capable of fractionating the samples based on the fine optical image of the sample and the distribution and localization of the fluorescence in the sample utilizing the microfabrication technology and easily analyzing/sorting the sample cells without damaging the samples retrieved (JP-A 2003-107099, JP-A 2004-85323, WO2004/101731). This apparatus is a substantially useful cell sorter for use in a laboratory, but for practical industrial/medical use, new techniques are required for the microfluidic pathway, cell transportation, retrieving method, and sample preparation.

[Non-Patent Document 1]
Kamarck, M. E., Methods Enzymol. Vol. 151, p 150-165 (1987)
[Non-Patent Document 2]
Micro Total Analysis, 98, pp. 77-80 (Kluwer Academic Publishers, 1998); Analytical Chemistry, 70, pp. 1909-1915 (1998)
[Patent Document 1]
JP-A 2003-107099
[Patent Document 2]
JP-A 2004-85323
[Patent Document 3]
WO2004/101731

SUMMARY OF THE INVENTION

It is an object of the present invention to establish a cell sorting chip and a cell sorting technique for positively detecting and sorting a predetermined cell for the purpose of cell sorting or detection using a flow path formed on a substrate, and to provide a cell analyzer/sorter using a chip inexpensive and replaceable for each sample.

When a micro flow path is formed on a substrate and fluid flows therethrough, the fluid flowing therethrough generally becomes a laminar flow. Although there seems not to be a fluid flow rate distribution in the direction of the perpendicular to the flow direction, when a cell suspension actually flows through such a micro flow path, a phenomenon actually occurs in which the cells reach to a wall in the flow path. Since the cells reach to the wall receive resistance against the flow, the flow rate near the wall lowers and the cells may contact other cells flowing from behind. When such a phenomenon occurs in a cell sorter or a flow cytometer, it is difficult to distinguish those connecting cells to sort and detect the cells. In order to avoid such a phenomenon, the sheath flow technique is used in general. This sheath flow technique is to array the cells in line by allowing the cell suspension to flow into a center of a fast-streaming flow of the fluid assumed to be a sheath, which is achieved by uniting a sheath flow to be the sheath and a core flow and discharging the same into the air as a jet stream. Having no wall in the first place, the conventional method can sort the cells under an ideal condition where the cells do not crash into the wall.

However, it is very difficult to stably form the jet stream using the sheath, a practical system is very expensive, and the cell for forming the sheath cannot be replaced for each sample. Not only concerning a large-sized system but also concerning a cell sorter formed on a chip, any of the conventional techniques except the method disclosed by the inventors of the present invention uses independent pumps for delivering the sample solution and for delivering the sheath fluid with no exception. These pumps are placed away from the chip, and need to be reconnected every time the chip is replaced. It is also necessary to readjust the balancing fluctuation between the sample fluid delivery speed and the sheath fluid delivery accompanied with the replacement of the chip. To perform such strict control, a large-sized and highly stable pressure-pump is required.

Since the cell sorter is fabricated on the chip, it is an important task to improve the usability and to reduce the cost by forming the fluid delivery section on the chip as well to perform all the functions except optical functions in the closed state only on the chip. The all-included cell sorter chip structure creates another simple and easy way to use up a cell sorter chip with respect to each sample. For instance, isolation of stem cells or a clinical laboratory test of cells require prevention of contamination with cells deriving from other specimen tissue, but the contamination does not have to be considered if the cell sorter chip is disposal for one-time use. It is a first object of the present invention to establish a cell sorting system without cross contamination essential to the medical field, especially to the field of the regeneration medicine, enabling a perfect prevention of the cross contamination due to the smaller size of the equipment, reduced cost, and replacement of the chip for each sample, by making the primary sections of the cell sorter in a chip, as described above.

One important technical issue to achieve the cell sorter on the chip is a sorting mechanism for cells flowing through the fine flow path. Various types of sorting mechanisms have been suggested. Examples of them include switching the flow path by ultra sound, a magnetic field, or a valve, and moving the cells in any given direction by optical trapping force, a high frequency alternating electric field, or a DC electric field. Among them, a mechanism that can achieve the sorting without damaging the cells, with high repeatability, and without a special device adopts a method using the DC electric field at a low voltage. However, in performing the cell sorting at a high speed using the DC electric field, if a normal metal electrode is used, the electrode is electrolyzed during sorting, and thus a stable long-time use is disadvantageously impossible. A method closest to the practical use is described in WO2004/101731.

WO2004/101731 discloses a cell sorter chip capable of mass production created using the microfabrication technology. This cell sorter chip sorts the cells in the electrophoretic state by impressing the DC electric field to the internal of the flow path through which the cells flow using a gel electrode as a mechanism sorting the cells in order to prevent an effect of the electrolyzation at a certain degree. As the gel electrode, for instance, an agarose gel containing electrolytes is used. Since only gel is present, through fine pores, in proximity to the flow path through which the cells flow, it is possible to prevent an effect of bubble production for a certain time, but which is not sufficient. There is another problem in that the gel is not suitable for a long-term storage due to the weakness for dryness, since the gel must be supplied and stored in a state containing the electrolytic buffer fluid. If the gel is frozen for long term storage, the gel is damaged from freezing, and therefore the storage in the frozen state is not possible.

Therefore, a second object of the present invention is to provide a gel electrode capable of preventing production of bubbles while the electric field is impressed thereto and being resistant to dryness and freezing during storage, and to provide a disposable cell sorter chip for each specimen in the real sense of the term.

In an attempt to sort the cells using the flow path formed on the substrate, an algorithm to recognize the cells in some way by providing a section for performing the cell recognition in a specific region in the flow path is required. In another attempt to use the cell sorter chip as a cell sorter sorting the cells, an sorting section must be provided downstream of a cell detecting section. There are three methods for detecting the cells as described below:

(1) The detecting section on the flow path is irradiated by light such as laser beams or the like, and detect the scattered light diffraction generated when a cell crosses or to detect fluorescence when the cells can be stained with the fluorescence.

(2) An electrode is provided in the detecting section to detect the change in impedance or conductance generated when the cell crosses the electrode.

(3) A CCD camera or the like is used to detect the cell as an image.

Since the cell recognition is substantially performed at one point in the method (1) so that the high-speed processing is possible even when the cells flow in succession at a high speed, this method is used in a large-sized cell sorter employing a technique to move the cell between the detecting section and the sorting section at a constant speed by encapsulating the cells in a droplet. The method (2) is also capable of high-speed processing, but it is generally employed by a flow cytometer used for cell sorting because of the incapability of measuring the speed of the cell moving after the detection and the difficulty of combining with a sorting mechanism. The method (3) appears simple at a glance, but it is not generally used in a cell sorter because of an increased load of image processing since it is necessary to process a plurality of cells constantly moving in the flow path.

However, in an attempt to perform the similar cell recognition and subsequent cell sorting in a flow path incorporated in a small area on the substrate, various problems may arise anew. At first, the moving speed of the cells flowing through the flow path is not the same, that is, it varies due to many elements such as the shape and size of the cell, and whether the cell flows in the center of the flow or near the wall. Therefore, especially the time after the cell is recognized until the cell is sorted downstream may fluctuate. Next, since the moving speeds of the cells are different from one another as described above, a phenomenon may appear in which a certain cell may forereach another cell in the flow path. Therefore, such problems should be solved when each cell must be ensured to be sorted in the methods 1) and 2) in which the cell is observed at one point. Now a third object of the present invention is to provide an algorithm to recognize cells flowing in the flow path in succession at a high speed and sort out necessary cells by detecting the cells as an image using a CCD camera or the like.

The conventional cell sorter is still enough to isolate a specific cell region, analyze the included genome and transcriptome, or perform an examination using immunochemistry. However, in many methods, retrieved cells have already terminated the biological functions thereof due to the operations such as staining and fixing. Therefore, it is disadvantageously difficult to analyze the dynamic functions of the retrieved cells and utilize the cells by cultivating the same. In particular, in order to obtain the cells as a material for regeneration medicine expected of the practical use thereof and pharmacokinetic examinations using a piece of cultivated tissue cells, it is important to establish a technique to dissect and retrieve an organ tissue at the cell level.

A fourth object of the present invention is to provide a chip device integrating a front-end processing section for isolating the cells from the surface of the organ tissue in sequence to roughly sort the cells with respect to each cell layer and a cell sorting region, and a cell sorting method using the same.

As described above, the present invention suggests, as a specific architecture for constructing a cell sorter or a flow cytometer on a chip, especially a form of the flow path for the cell and a structure of a cell suspension delivery section, a structure of the electrode section capable of tolerating a long-term storage and entering a distribution channel, a sorting algorithm, and a cell measuring and sorting chip from a piece of tissue or a mass of cells as a sample.

The cells assumed in the present invention ranges from a bacterium at the smallest to an animal cell such as a cancer cell at the largest. Therefore, the size of the cell ranges approximately from 0.5 to 30 μm. To perform the cell sorting using a flow path incorporated in a substrate, the first problem is a width of the flow path (cross-sectional dimension). The flow path is assumed to be formed in a space of approximately 10 to 100 μm in the thickness direction of the substrate substantially in a two-dimensional plane. Based on the size of the cell, the suitable size would be 5 to 10 μm for the bacteria, and 10 to 50 μm for the animal cells. As described above, it is necessary at first to prevent the cells from attaching onto the wall. Another fluid is run as bypass flows from both sides of the flow path through which the cell suspension flows so that the cells do not attaching onto the wall. As a result of considering such a method of confluence of the fluids, it was found to be most effective when the width (substantially a cross-sectional area) of the flow path through which the cell suspension flows before confluence with the two side fluid flows is almost equal to the width of the flow path after the confluence, and also the two side fluid flow paths running in together from the both sides have the same flow path lengths to maintain the same pressure. A wider flow path after the confluence may reduce an effect of keeping the cells away from the wall. A narrower flow path after the confluence excessively may accelerate the speed of the cell flowing after the confluence to make it difficult to detect the cells, and to extremely lower the frequency of the cells passing by. Also, since the resistance in the flow path may vary if the two side fluid flows have different lengths, the central fluid flow path allowing the cells to flow may be disadvantageously pushed to either side.

To establish a cell sorter or a flow cytometer on a chip, controlling the flow rates of the cell suspension or the another buffer fluid flows arises as a very difficult problem. The problem can be solved by using a large-sized pump without a pulsating flow, especially capable of producing a stable flow rate of several tens picoliter/min. Assuming a disposal chip, however, the chip must be connected to the pump every time a new chip is used, which is disadvantageous in terms of repeatability and usability. While a study is made to incorporate the pump onto the chip, the present invention solves the problem by free fall of the fluid without using any pump. Specifically, a minute amount of delivery fluid without the pulsating flow is achieved by providing a reservoir at an entrance of the flow path to make the fluid level at an exit of the flow path lower than the fluid level in the reservoir.

With such a system using the difference in the fluid levels, it is difficult to control the fluid flow rate when a plurality of fluids are delivered. The ratio of the fluid flow rates between the cell suspension and the other buffer fluid flow may disadvantageously vary with a slight difference in the fluid level (height). With the present invention, the levels of the both fluids are accurately equally controlled to solve the problem by combining the reservoir containing the cell suspension connected to the sample flow pathway, and the reservoir containing the buffer fluid connected to the other buffer fluid flow. That is to say, the fluctuation in the flow rates between the cell suspension flow and the other buffer flow is equally adjusted by delivering the same height of fluid in the combined buffer reserver as a driving force. For the reservoir structured as described above, there is suggested a structure having partitions in the reservoir, a flow path for the sample being connected to one bottom of partitions, and another buffer flow path for the buffer fluid flow being connected to the other partition. It is considered that the fluid levels (heights) of partitions in the reservoir are substantially aligned with each other by the principle of the siphon effect. While the buffer fluid is not separated in the reservoir on the partitions of the starting points of sample fluid flow pathway and buffer fluid flow pathway at the bottom of the reservoir, the cell suspension will not flow into the buffer flow beyond the walls of partitions since the cell has heavier than that of the buffer fluid.

Based on the present invention, the detecting section is disposed at the flow path section where the buffer flow joins together with sample flow. A section is provided for observing the flow path section after the confluence using a CCD camera, and a cell sorting region is provided downstream thereof as needed. "As needed" means use of the chip as a cell sorter, and as a flow cytometer, a drain is directly provided downstream of the detecting section. This allows the cells to flow along a path at the center of the flow path at a substantially constant speed without crashing into the wall.

To be used as a cell sorter, a cell sorting region is provided downstream of the detecting section. A flow path used to move the cells at the entrance of the sorting section joins together with a flow path allowing only the buffer fluid (or a culture medium) to flow at the cell sorting region, and branches off therefrom on the downstream side. To sort the cells at the sorting section, a set of electrodes are provided in the cell sorting region as a unit for moving the cells by applying external force to the cells from the outside, and a flow path capable of sorting and discharging the cells is provided. When the posture control (change of the flow path) is performed on the cell in the flow path by applying voltage to the electrodes and thus by causing ions to flow, the cells move in the direction of the synthetic vector of the direction in which the ions flow and the direction in which the fluid flows in the flow path. Because of negatively charged, the cells move toward the positive electrode. Therefore, the synthetic vector for moving is controlled by placing the electrode with an anode shifted to the downstream side and a cathode shifted to the upstream side of the direction in which the flow path flows after the confluence, enabling the change of the flow path of the cells with a low current. Cells changed for the flow paths and cells not changed for the flow path flow into respective separate flow paths to be sorted out. Herein, the flow path where the sample flows is the flow path in which the original flow path for the sample is combined with the bypass flow. On the contrary, the bypass flow does not join on the upstream side together with the flow path in which only the buffer fluid (or culture medium) to be joined flows. The sample flow path, the flow path for only the buffer fluid, and the flow path after the confluence have the same width. The sample flow path after the confluence has a faster flow rate by the increased amount of the buffer flows, whereby the flow runs off slightly into the flow from the buffer fluid flow path side at the branch point. This is also an important effect to facilitate controlling the posture of the cells and switching from the sample flow path side to the buffer fluid flow path side. Since the cells flow in the center of the sample flow path side when the current is not applied, the cells flow to the side of the flow path to which the samples flow without switching.

The electrode disposed in the sorting section is configured to contact the metal electrode with a space filled with gel via a liquid junction (a tubule including a space and a fluid filling the space, which is filled with gel). Hereinafter this is referred to as a gel electrode. The gel electrode is made of a gel matrix in which the cathode includes a buffer fluid with low pH to absorb a generated hydroxyl ion and the anode includes a buffer fluid with higher pH to absorb a generated hydrogen ion. The gel matrix can use a meshwork gel commonly used in biochemistry such as agarose and polyacrylamide. This suppresses the production of gas due to the electrolyzation of the gel electrode section, enabling a stable cell analysis/sorting. Needless to say, since the metal electrode does not come into direct contact with the cells, the surface of the electrode hardly damages the cells. It is possible to prevent any damage to the sample cells and to prevent the electrode from losing due to the electrolyzation.

As described above, the gel electrode is more advantageous than the metal electrode disclosed in JP-A 2003-107099, but there still remains a problem in supplying a user with the chips. Specifically, since the gel electrode has poor storage stability due to the nature of the wet electrode, a user is substantially required to fill the chip with the gel before use to prepare the gel electrode. The present invention enables the storage at room temperature for a certain period by adding a nonreducing disaccharide such as trehalose, glycerol, or ethylene glycol. Further, while a long-term frozen storage of a gel is normally difficult because the gel structure is destroyed by freezing, quick freezing the gel with the trehalose and the like as described above can suppress appearance of ice crystals destroying the gel structure, and accordingly enables the long-term storage of the gel electrode by frozen storage.

Furthermore, the cell sorter according to the present invention may have a unit for preventing clogging of the flow path by capturing impurities upstream of the flow path where a fluid including the sample introduced into the cell sorting region is introduced.

In short, the present invention provides a cell sorter including a space for sorting cells, at least one flow path into which a fluid including cells is injected, at least two flow paths used for discharging the fluid, and a unit for applying an external force to the cells from the outside of the cell sorting region, wherein the flow paths are placed so that the cells are discharged from the cell sorting space to respective different flow paths when the external force is and is not applied from the outside to the cell sorting region.

This cell sorter reduces any damage to the cells because the external force is applied to the cells from the outside of the cell sorting region to prevent the electrode and the like from coming into direct contact with the buffer fluid including the cells and the cells are sorted by applying a current at a low voltage (namely, by supplying ions).

The algorithm of the recognition and sorting of the cells have the following features.

Since the cell recognition at one point is impossible for the reasons described above, the sell sorting is further ensured by enlarging the measuring range to a plane to recognize the cells by the image recognition and by tracking the same. What is important in this step is a speed of taking the image. A camera with a common video rate of 30 frames/sec. may miss some cells by the image. With an image taking rate of at least 200 frames/sec., it is possible to recognize the cells flowing in the flow path at a relatively high speed.

Next, in the image processing method, the fast image-taking rate indicates difficulty in processing a very intricate image. Concerning the cell recognition at first, as described above, the moving speed of a cell varies from cell to cell, and there is a possibility of forereaching another cell. Therefore, when each cell appears on an image frame for the first time, the cell is numbered and managed with the same number until the cell disappears from the image frame. In other words, a moving state of the cell image is managed by the number using a plurality of successive frames. The cells in the successive frames are linked on the condition where the cells move downstream in the order starting from the cell on the upstream side in each frame and where the moving speed of a certain cell numbered and recognized in the image is within a certain range. Thus, even if any cell forereaches another, it is possible to track each cell without fail.

Now it is possible to recognize the cells. For numbering of a cell, the cell image is binarized and the barycenter thereof is computed. A luminance barycenter, an area, a perimeter, a long diameter and a short diameter of the binarized cell are computed, and each cell is numbered using these parameters. It should be possible to automatically record the images of each cell as image data at this timing, which is advantageous for the user.

Next, in use for cell sorting, only a specific cell must be sorted among the numbered cells. The index of the sorting may be such information as the luminance barycenter, area, perimeter, long diameter and short diameter as described above, or other information may be obtained by the fluorescence detection in the detecting section and an image processing section. In any case, the cell obtained in the detecting section is sorted according to the numbering. More specifically, the moving speed (V) of the numbered cell is computed based on the images taken in at a predetermined interval, a distance from the detecting section to the sorting section is assumed to be (L) against the cell moving speed (V), and an impression timing is assumed to be between (L/V) and (L/V+T) depending on the impression time (T), whereby the cells are electrically sorted out when a cell with a target number comes between the electrodes.

In general, in the cells of an animal tissue, there is an extracellular matrix between cells so that the cells do not separate from one another. The extracellular matrix is formed with a meshwork coupling an aggregation of protein and polysaccharide secreted from surrounding cells with the surface of the cells secreting the same. Material of the extracellular matrix includes proteoglucan, collagen elastin, fibronectin, and laminin. Therefore, to obtain each cell forming the tissue, the protease processing such as trypsin is generally performed. In general, the trypsin processing is performed for a short time after dissection of the tissue into as small pieces as possible so that a single cell can be obtained without giving any damage to the cell.

Making use of the protease processing, the present invention also provides a chip having a function and structure of obtaining a series of cells distributing in the depth direction of tissue by isolating the cells from the surface of the tissue sequentially by the protease processing.

DESCRIPTION OF THE PREFERRED EMBODIMENTS (First Embodiment)

Figure 1:
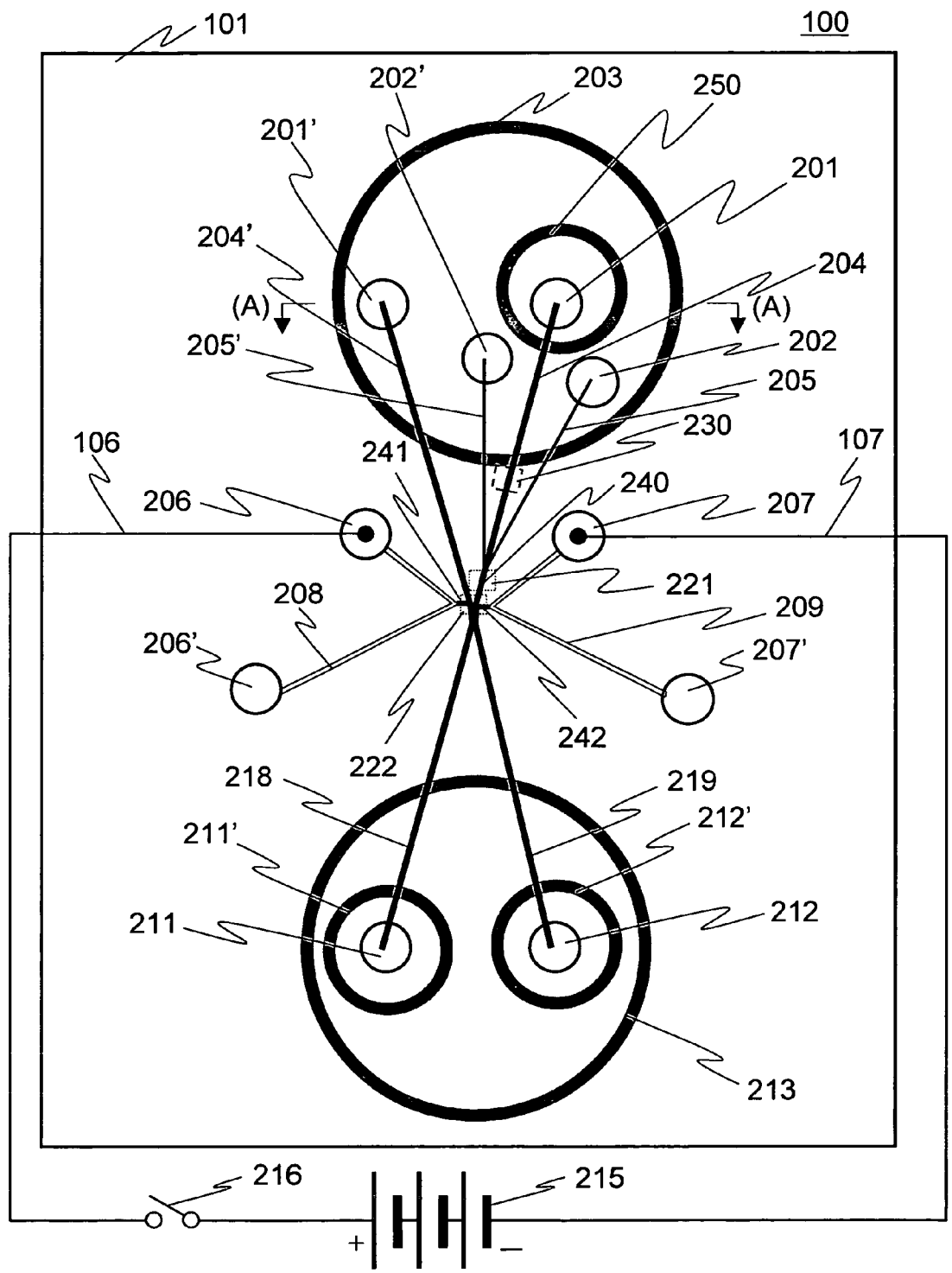
FIG. 1 is a plan view schematically showing one example of system configuration of a cell sorter according to the present invention.

FIG. 1 is a plan view schematically showing one example of system configuration of a cell sorter according to the present invention. A cell sorter 100 includes a substrate 101. The substrate 101 has a flow path provided on the bottom surface and an opening communicating with the flow path provided on the top surface, and the opening functions as a port for supplying a sample or a necessary buffer fluid. Furthermore, a reservoir is provided for supplying a sufficient quantity of buffer fluid and also for controlling a flow rate in each flow path. The flow paths can be prepared by means of the so-called injection molding in which plastics such as PMMA is injected into a metal mold. The chip substrate 101 has the size of 20×30×1 mm (t) as a whole. To form grooves and through holes engraved on the bottom surface of the substrate 101 into flow paths and wells, a laminate film with a thickness of 0.1 mm is thermally applied to the bottom surface with the grooves engraved thereon. Cells flowing in the flow path can be observed with an object lens having an aperture number of 1.4 and magnification of 100 times through the laminate film with a thickness of 0.1 mm. Needless to say, the cells can easily be observed with a lens having a lower magnification. Provided on the top surface of the chip substrate 101 are a hole 201 used for introducing a sample buffer liquid containing cells into a micro flow path, holes 201', 202, and 202' used for introducing a buffer fluid not containing any cell, and a reservoir 203 used for managing the holes above. Therefore, when a sufficient quantity of buffer fluid is supplied into the reservoir 203, the holes 201, 201', 202, and 202' communicate with each other with the buffer fluid. Because of the configuration, a buffer fluid is supplied to the flow path 204 and flow path 204' communicating with the holes 201 and 201', respectively, up to the same fluid level. Therefore, when a width or a cross section, and furthermore a length of the two flow paths are substantially equalized (assuming that heights of the flow paths are the same), flow rates in the two flow paths can be set to substantially the same level. Similarly a buffer fluid can be supplied into the flow paths 205, 205' communicating with the holes 202, 202', respectively, up to the same fluid level, and furthermore a flow rate of a buffer fluid flowing through the flow paths 205, 205' can be set to a predetermined ratio relative to a flow rate of a buffer fluid flowing through the flow path 204. Provided around the hole 201 for introducing a buffer fluid containing a sample is a wall 250 for preventing diffusion of the sample buffer fluid containing cells. The height of the wall 250 is lower than the wall of the reservoir 203, and the buffer fluid is filled up to a level higher than the wall 250.

The buffer fluid containing cells introduced into the hole 201 passes the micro flow path (20 μm in width and 15 μm in depth) and is introduced to a cell detecting region 221 and a cell sorting region 222. A filter 230 directly incorporated as a minute structure in the chip is provided on the micro flow path 204 to prevent clogging therein. On the other hand, the buffer fluid not containing any cell introduced into the holes 202, 202' passes through the flow paths 205, 205', respectively, (12 μm in width and 15 μm in depth) and comes in the buffer fluid containing cells in the micro flow path 204. Reference numeral 240 indicates a micro flow path after the confluence, which functions as a cell detecting region 221. Further the micro flow path 240 is introduced into a cell sorting region 222.

The buffer fluid not containing any cell introduced into the hole 201' passes through the micro flow path 204' (20 μm in width and 15 µm in depth) and is introduced into the cell sorting region 222, where the buffer fluid comes into the micro flow path 240. A width of the flow path after the confluence is described below. The joined flow path after the confluence branches into a micro flow path 218 (20 µm in width and 15 µm in depth) and a micro flow path 219 (20 µm in width and 15 µm in depth) at an exit of the cell sorting region 222.

Reference numerals 206, 206' and 207, 207' denote holes each for introducing gel containing electrolytes. The gel introduced into the holes 206 and 207 are fed into the holes 206' and 207' through the micro structures 208, 209, respectively, on the bottom surface of the substrate 101 (a bent groove with a width of 200 µm and a height of 15 µm). Therefore the micro structures 208, 209 are filled with gel containing electrolytes. Curved sections of the micro structures 208, 209 are coupling sections 241, 242 with the micro flow paths 204, 204', respectively, each having a fluid path structure with a length of about 20 µm, and in the cell sorting area 222. With this configuration, the gel can come into direct contact with the buffer fluid flowing in a flow path 247 formed by the confluence of the micro flow path 240 and micro flow path 204'. An area where the gel and buffer fluid contact each other is 15 µm (the length along the flow path)×15 µm (height). Electrodes each indicated by a black circle is inserted into the holes 206 and 207 into which the gel is introduced, and the electrodes are connected via wiring 106, 107, respectively, and a switch 216 to a power supply 215. The switch 216 is turned ON only when a voltage is loaded to a buffer fluid flowing the flow path 247 formed by the confluence of the micro flow path 240 and micro flow path 204'.

In the coupling sections 241 and 242, the gel comes into contact with the buffer fluid flowing through the flow path 247 formed by the confluence of the micro flow path 240 and micro flow path 204' in the cell sorting area 222. As shown in the figure, in the flow path 247 the coupling section 241 where gel comes into contact with the buffer fluid is located upstream of the coupling section 242 where gel comes into contact with the buffer fluid. When a plus voltage is loaded to the electrode in the hole 206 and a minus voltage to the electrode in the hole 207, cells flowing in the micro flow path 240 can be migrated more efficiently into the flow path 211'. The reason is that, when a current is applied, an electrophoretic force is loaded to cells charged in the minus state to generate a synthesized vector of a vector received from this force and the buffer fluid flowing in the flow path and that of the electrophoretic force. This can utilize an electric field with a high degree of efficiency as compared to a case where the coupling sections 241 and 242 are prepared at the same positions with respect to a flow in the flow oath (at symmetric positions relative to the flow). Consequently, migration of cells into a micro flow path 218 or a micro flow path 219 can be stably realized with a lower voltage.

Recovery holes 211, 212 used for recovering cells sorted in the cell sorting region 222 are provided in downstream sections of the micro flow paths 218, 219, respectively. Walls 211', 212' are provided for the holes 211, 212, respectively, in order to prevent diffusion of a buffer fluid containing the recovered cells, and furthermore a reservoir 213 for management of the holes is provided. Height of the reservoir 213 is greater than those of the walls 211', 212' for preventing diffusion of a buffer fluid containing the recovered cells. The buffer fluid is filled up to a position higher than the walls 211', 212' before the sorting operation, but the height is lower than a level of the buffer fluid filled in the reservoir 203.

Since a surface level of the buffer fluid in the reservoir 203 is higher than that in the reservoir 213, this head drop generates a driving force for moving the buffer fluid flowing in the flow path, and also generate a stable flow without pulsation. When a capacity of the reservoir 213 for storing the buffer fluid is sufficiently large, all of the buffer fluid containing cells and introduced into the hole 201 can be supplied to the flow path 204.

Figure 2:
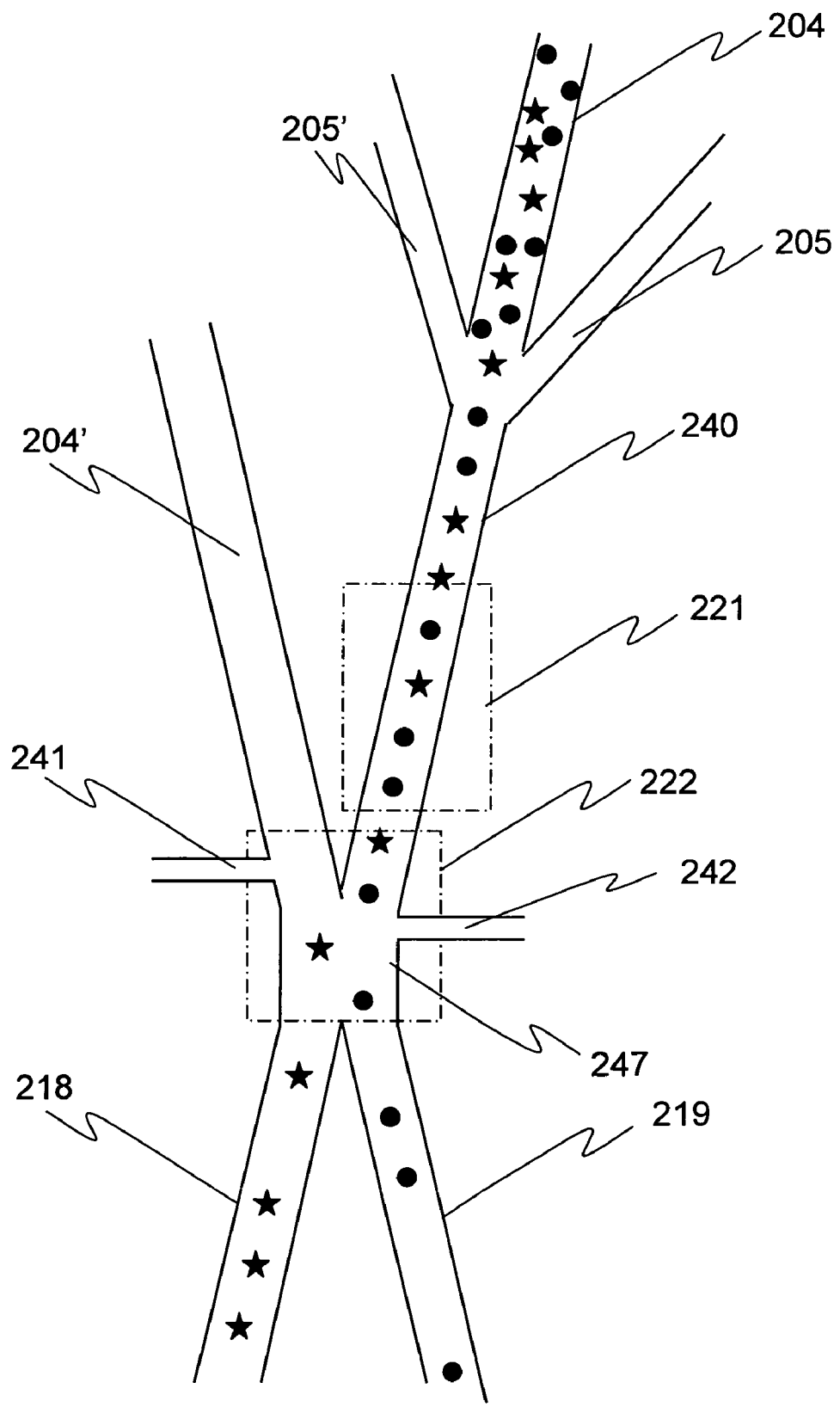
FIG. 2 is a view illustrating the state in which buffer fluids in micro flow paths 205 and 205' join into a buffer fluid containing cells in a micro flow path 204, the joined fluid flows down the micro flow path 240, then the joined fluid joins into the buffer fluid flowing down the micro flow path 204' at a position just ahead the cell detecting region 221 and flows down the micro flow path 240.

FIG. 2 is a diagram for illustrating the state in which the buffer fluids in the micro flow paths 205, 205' come into the buffer fluid containing cells in the micro flow path 204 to form the cell detecting region 221, and further flow down the micro flow path 240 to come into the buffer fluid flowing down the micro flow path 204', and further flows down the micro flow path 247 to form the cell sorting region 222.

A description will be made of the reason why the buffer fluids not containing any cell flowing in the flow paths 205, 205' are joined into the buffer fluid containing cells flowing in the micro flow path 204 in the upstream section of the cell detecting region 221. The flow paths 205, 205' in which the buffer fluid not containing any cell flows are joined into the flow 204 in which the buffer fluid containing cells flows in the upstream section of the cell detecting region 221. However, the holes 201, 202, 202' provided in the utmost upstream sections of the respective flow paths communicate with the reservoir 203 storing therein the buffer fluid having the common fluid level. Because heights of the flow paths are the same, flow rates of the buffer fluids flowing in the respective flow paths are proportional to widths of the flow paths. The buffer fluids join together, and it is assumed that a width of the flow path 240 after the confluence is substantially equal to that of the flow path 204 in which the buffer fluid containing cells flows. The expression of "substantially equal" as used herein means that the two widths are substantially equal to each other when the machining precision is taken into consideration, and the expression does not always means that the two widths are exactly equal to each other. With the configuration, the buffer fluid flowing down the flow path 204 is pushed toward the central portion at a constant ratio by the buffer fluids flowing down the flow paths 205, 205', and therefore cells colliding the side walls while flowing in the flow path 204 do not collide the side wall of the flow path 240 after the confluence.

In the micro flow path 247 in the cell sorting region 222, the buffer fluids flow down the flow path 240 and flow path 204' as if they keep the flow layers, respectively, and have the same width. Cells flowing down the flow path 204 in the cell detecting region 221 are detected, and in the cell sorting region 222 the cells are sorted by loading an electric field to the cells with the coupling sections 241 and 242 where the gel contacts the buffer fluids flowing down.

Figure 3:
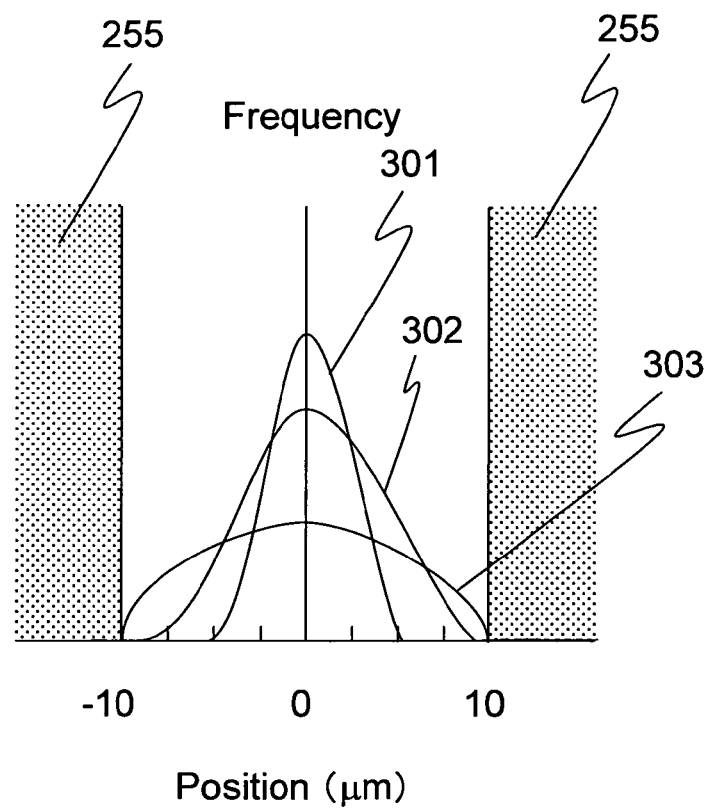
FIG. 3 is a diagram illustrating cell distribution in the flow path 240 after the confluence as a result of movement of the buffer fluid flowing down the flow path 204 toward a central section caused by the flow paths 205, 205'.

FIG. 3 is a diagram showing distribution of cells in the flow path 240 after the confluence as a result of movement of the buffer fluid flowing down the flow path 204 pressed by the buffer fluid flowing down the flow paths 205, 205' toward the central portion on the cell detecting region 221. Reference numeral 255 denotes a side wall of a flow path. In other words, this diagram shows the state in which a flow of a buffer fluid containing cells flowing down the flow path 204 with a width of 20 µm is pushed toward a central portion of the flow path 240 with a width of 20 µm by flows of the buffer fluids flowing down the flow paths 205, 205' each having a width of 12 µm. In addition, this view is plotted with the horizontal axis indicating a position of the flow path 204 and the vertical axis indicating a frequency of appearance of cells. A curve 301 indicates that, when quantities of the cells in the buffer fluids flowing down each of the flow paths 205, 205' are substantially a half of the cells in the buffer fluid flowing down the flow path 204, that is, when a width of each of the flow paths 205, 205' is substantially a half of the flow path 204, the cells are distributed in the area with the width of about 10 µm in the central portion. A curve 302 shows distribution of cells when a width of each of the flow paths 205, 205' is smaller, while a curve 303 shows distribution of cells in a case where the flow paths 205, 205' are not provided. As clearly understood from the curve 301, by setting widths of the flow paths 205, 205' to appropriate values respectively, it is possible to substantially separate the cells from walls of the flow paths and prevent the cells from colliding the side walls.

Although not described in relation to FIG. 3, the flow path 240 and the flow path 204' join together in the cell sorting region 222. Therefore, FIG. 3 shows the tendency in which the buffer fluid spreads, to a certain degree, in the direction where the flow path 204' extends, but the buffer fluids flowing down the flow path 204 and flow path 204' keep the flow layers respectively, so that any change does not occur substantially.

In the description above, it is assumed in FIG. 1 that the flow paths 204, 204', 205, and 205' have the same width along the full length. However, when it is required to lower resistance by a flow path, the width can be widen in an area close to the reservoir 203. Furthermore, a width of a flow path required to realize desired distribution of cells must be kept at the correct value along the length of, for instance, about 100 µm, and therefore an area with a large width may be long in consideration for the resistance of the flow path. For instance, a width of the flow path 205 forming a side flow in which a buffer fluid not containing any cell flows may be made larger as compared to that of the flow path 204 in which a buffer fluid containing cells flows and also a length where the width is to be fixed at a constant value may be made shorter. In this case, the resistance of the flow path 205 as a side flow path becomes smaller as compared to that in the flow path 204. As a result, a width of a flow of fluid from the flow path 204 is operatively reduced in the flow path 240 after convergence. That is to say, a cell distribution curve in FIG. 3 becomes sharper.

Figure 4:
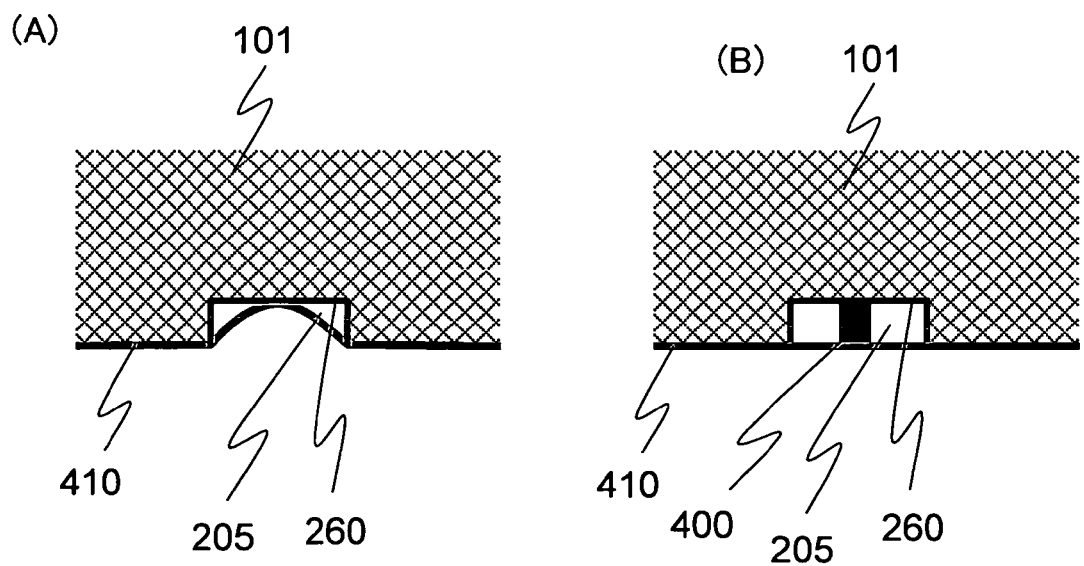
FIGS. 4(A) and 4(B) are cross-sectional views illustrating a problem associated with widening of a flow path and an example of solution for the problem, respectively.

FIGS. 4(A) and 4(B) are cross-sectional views for illustrating a problem associated with widening of a flow path width and a solution to the problem, respectively. In the figures, reference numeral 101 denotes a substrate, 260 denotes a groove formed on the substrate, and 410 denotes a laminate film covering the groove 260. Reference numeral 205 denotes a flow path, which is formed of the groove 260 and a laminate film 410 covering the groove 260. As shown in FIG. 4(A), if a width of a flow path is made larger, when a laminate film is pressure bonded to the substrate 101, sometimes the laminate film 410 may fall in the groove 260 in a portion having the larger width of the flow path 205, which may in turn cause clogging of the flow path 205. In contrast, in FIG. 4(B), a beam 400 is formed in the larger width portion of the groove 260. By providing the beam 400, it is possible to prevent the laminate film from falling in the groove 260 to clog the flow path 205.

Figure 5:
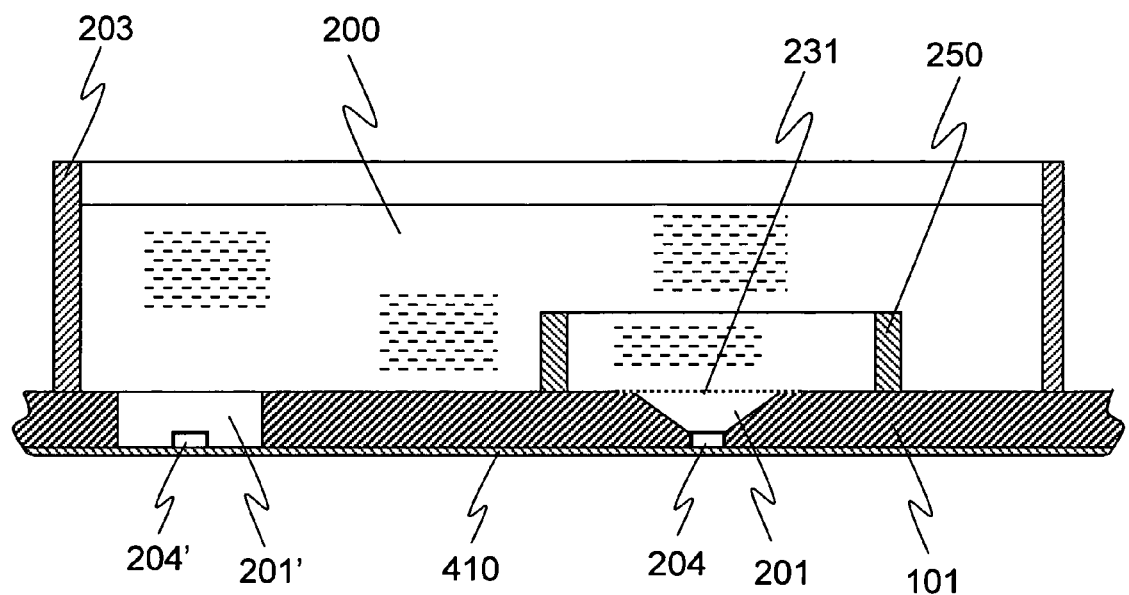
FIG. 5 is a cross-sectional view illustrating details of a reservoir 203, openings 201, 201', and flow paths 204, 204' described in FIG. 4 taken along line A-A in FIG. 1 and shown in the direction indicated by the arrowheads.

FIG. 5 is a cross-sectional view taken along line A-A in FIG. 1, as viewed in the direction indicated by the arrowheads. FIG. 5 illustrates the reservoir 203, openings 201, 201' and flow paths 204, 204' shown in FIG. 4 in more details. Respective grooves corresponding to the micro flow paths 204, 204' are formed on a bottom surface of the chip substrate 101 and are covered with the laminate film 410 to form the micro flow paths 204, 204. A hole 201 used to introduce a buffer fluid containing cells in the micro flow path is provided in the uppermost upstream portion of the micro flow path 204. In addition, a hole 201' used to introduce a buffer fluid not containing any cell flows is provided in the uppermost upstream portion of the micro flow path 204'. A wall or a reservoir 250 for preventing dispersion of a sample buffer fluid containing cells injected into the hole 201 is provided to surround the hole 201. Also the wall or reservoir 250 for preventing dispersion of a sample buffer fluid containing cells injected into the hole 201' and hole 201, and furthermore the holes 202, 202' not shown in FIG. 5 are provided inside the reservoir 203. The reservoir 203 is filled with a buffer fluid 200, and the buffer fluid 200 is supplied to all of the holes, so that respective flow rates of the buffer fluids flowing down the micro flow paths 204, 204' can substantially be equalized to each other. In addition, respective flow rates of the buffer fluids flowing down the micro flow paths 205, 205' can substantially be equalized to each other. Further a ratio of a flow rate of the buffer fluid flowing down the micro flow path 204 to a flow rate of the buffer fluid flowing down the micro flow path 205 can stably be maintained at a specified value. The hole 201 is cone-shaped for sample cells to be introduced into the flow path 204 without fail. The wall 250 may be a short compact reservoir provided in the reservoir 203 as shown in FIG. 1, or may have a structure like a partition wall. Reference numeral 231 denotes a membrane filter, which is provided on an upper surface of the hole 201 for removing dust contained in the sample. Dispersion of cells can be prevented by providing the wall 250, so that it is not necessary to directly inject a sample buffer fluid containing cells into the hole 201.

The structure in which a commonly available reservoir is provided in the uppermost upstream section of each flow path is one of core features of the present invention. With the structure ensuring a common liquid level, it is possible to feed buffer fluids at the same pressure into a plurality of flow paths, so that the most simple fluid feed system capable of being incorporated on a substrate is provided. Further to differentiate fluids fed through a plurality of flow paths, various types of buffer fluids are separated by partition walls each having a height lower than the liquid surface, and with this structure, it is possible to feed various types of buffer fluids at the same pressure into different flow paths. If buffer fluids each having a higher specific gravity as compared to buffer fluids with a common fluid level is used as the buffer fluids separated by partition walls, the buffer fluids do not substantially mix together. Furthermore, because cells have generally high specific gravities and sink on a bottom surface of a container, basically there occurs no problem. In treating chemotactic cells, it is necessary only to employ a partition wall over which the cells can not migrate. For instance, neuronal cells can not move over a wall (partition wall) with a height of only tens micrometers. Such cells as those of coli bacteria can be prevented from going into another flow path by providing a sponge-like film allowing free passage of a buffer fluid but inhibiting passage of cells.

(Second Embodiment)

A gel electrode is described in detail below. A gel electrode section includes holes 206, 206' and 207, 207', a microstructure 208 connecting the holes 206, 206' to each other, a microstructure 209 connecting the holes 207, 207' to each other, and coupling sections 241, 242 based on a structure allowing liquid communication in the cell sorting region 222, as shown in FIG. 1. When a chip is prepared by means of injection molding, no gel is included in the gel electrode section. The following description assumes use of agarose gel containing an electrolyte as an electrolytic solution. The gel is prepared such that a 0.25M NaCl-0.296M sodium phosphate (pH 6.0) buffer fluid is used for forming the minus electrodes 209, 242, and 1% agarose gel containing 0.25M NaCl-0.282M sodium phosphate (pH 8.0) is used for forming the plus electrodes 208, 241. The pH is differentiated to prevent generation of bubbles in association with electrolysis when a current is supplied. Hydrogen ions generated on the plus electrode side are neutralized by the buffer fluid having higher pH before they form hydrogen molecules, while the hydroxyl ions generated on the minus electrode side are neutralized by the buffer fluid having lower pH to prevent generation of oxygen molecules.

The gel electrode is preferably made of a gelatinous material including saccharide. In this case, the saccharide includes non-reductive disaccharide with a content of 3 to 50%, trehalose with a content of 1 to 50%, glycerol with a content of 5 to 30%, ethylene glycol with a content of 5 to 40%, or dimethyl sulfoxide with a content of 5 to 30%.

The following description assumes a case where a chip is prepared by means of injection molding, a cell sorter chip with gel electrodes is completed by injecting gel from the hole 206 and hole 207 and then the chip is left unused. The gel comes into contact with the atmospheric air in the open portions of the hole 206, 206', 207, and 207', and also in the coupling sections 241, 242 between the flow paths and the structure for liquid communication in the cell sorting region 222. Consequently, the gel starts to dry from the sections. The following devise is required to store the cell sorter chip with gel electrodes as it is in the prepared state. At first, drying from the holes 206, 206', 207, and 207' can be prevented by applying a seal on the opening sections until just start of use of the chip. The gel in the coupling sections 241, 242 between the flow paths and the structure for liquid communication in the cell sorting region 222 can be easily stored at 4° C. for about four months by storing the chip in an air-tight container together with a sheet containing water to prevent the gel from drying. A laminate bag is preferable as the air-tight container to reduce the air as much as possible.

A moisturizing agent is added to the gel for preventing the gel from drying and also for enabling long term storage of the gel. As the moisturizing agent, for instance, disaccharide such as trehalose or sucrose with a content of 1 to 10% or oligosaccharide, or glycerin with a content of 5 to about 10% can advantageously be used to prevent the gel from drying.

To store the gel for a longer term, it is preferable to put a cell sorter chip with gel electrodes in a laminate bag and refrigerate the chip in the state. In this step, ice crystals are generated when freezing and melting the cell sorter chip to destroy the gel structure. When ice crystals are generated around the gel electrodes which are prepared in a minute area such as a cell sorter chip, the sections becomes voids after melting. When the voids are produced and an electric field is loaded to the electrodes, sometimes cells may enter the voids, or the cells having entered the voids may leak into the flow paths on the cell sorter although not required, which is disadvantageous.

To prevent this phenomenon, a substance capable of suppressing growth of ice crystals is added to the gel in the gel electrode sections for enabling long term storage of the cell sorter chip in the frozen state, which is the most important feature of the present invention. The moisturizing materials as described above can be used as substances for suppressing growth of ice crystals. It is most effective to mix a disaccharide such as trehalose or sucrose or oligosaccharide when the gel is prepared. Of these materials, trehalose is extremely effective because the function to general animal cells is small. Its concentration may be 1%. The upper limit of the concentration is around 50%. Also sucrose is effective, but sucrose may be biologically functional to animal cells, and sometimes it may be inappropriate to use sucrose. It is possible to keep the capability of preventing refrigeration and reduce the biochemical influence by replacing a portion of a hydroxyl group in the sugar chain with a sulfuric group, so that it is advisable to introduce a sulfuric group into the hydroxyl group of the disaccharide. In addition, also such saccharide as glycerin and ethylene glycol are effective. Also dimethyl sulfoxide is effective, but sometimes ethylene glycol and dimethyl sulfoxide may cause problems in relation to the cytotoxity. In general, since a quantity of dimethyl sulfoxide eluted to the cell sorting flow path is very minute, the cytotoxity can be ignored.

A specific example is described below. A cathode electrolytic solution and an anode electrolytic solution each as described below are melted in an electronic oven by heating to convert into buffer fluids. The substrate 101 is placed on a heated hot plate heated to 60° C. and heated thereon. The cathode electrolytic solution and anode electrolytic solution having converted into the buffer fluids are injected to the holes 206, 207 with a syringe, sucked from the holes 206' and 207', and are filled in the microstructures 208, 209 as well as in the coupling sections 241 and 242. The melted gel enters the coupling sections 241 and 242 because of the capillary phenomenon. When left at room temperature for 10 minutes, the buffer fluids in the microstructures 208, 209 and the coupling sections 222, 242 are gelatinized. Since the flow path 247 has a larger cross-sectional area as compared to those of the coupling sections 241 and 242, the gelatinized buffer fluids never enter the flow path 247.

The improved gel composition is described below.

Minus electrode fluid: 1% trehalose, 0.25M Nacl, 0.296M sodium phosphate (pH 6.o), 1% agarose Plus electrode fluid: 1% trehalose, 025M Nacl, 0.282M sodium phosphate (pH 8.0), 1% agarose A surface of the cell sorter chip with gel electrode prepared as described above is sealed with an adhesive tape. Plasame which is a porous plastic towel is steeped in water, a 2 cm×2 cm piece of the towel that has been wrung is placed in a plastic bag with the size of 30 mm×40 mm together with the cell sorter chip with gel electrode and opening of the bag is closed with a sealer.

The chip is stored in this state at 4° C. or −20° C.

States of the gel electrode sections of the chip just after preparation and just before refrigeration, in 1, 3, and 6 months after start of storage at 4° C. and −20° C. are observed under a microscope. Furthermore, a culture liquid is added to the reservoir 203 to fill the buffer fluid into flow paths 204, 205, 205' with erythrocytes added in the hole 201, and it is checked that the cells are sorted to the flow paths 218, 219 by loading a voltage to the electrodes or cutting the electrodes. At first, in the chip just after the preparation, since the microstructures 208, 209 and coupling sections 241, 242 are filled with the gel, there is not external damage such as clacking or drying. When an electric field is applied to the gel electrodes, erythrocytes flowing down the flow paths in the cell sorting region 222 migrate to the flow path 219, and are stored in a reservoir 212' via the hole 212. When a voltage is not loaded thereto, the erythrocytes are deposited in the reservoir 211'. The cells reserved in the frozen state can be collected in the reservoir 212 by loading a voltage to the gel electrodes like in just after the preparation and in the reservoir 211 by shutting down the electric field. When the gel electrode section stored at 4° C. is observed under a microscope after the three months, the gel shifts backward in the coupling sections 108 and 109, but when the cells are actually supplied to flow, the separation is possible in the same manner as that just after the preparation.

Figure 6:
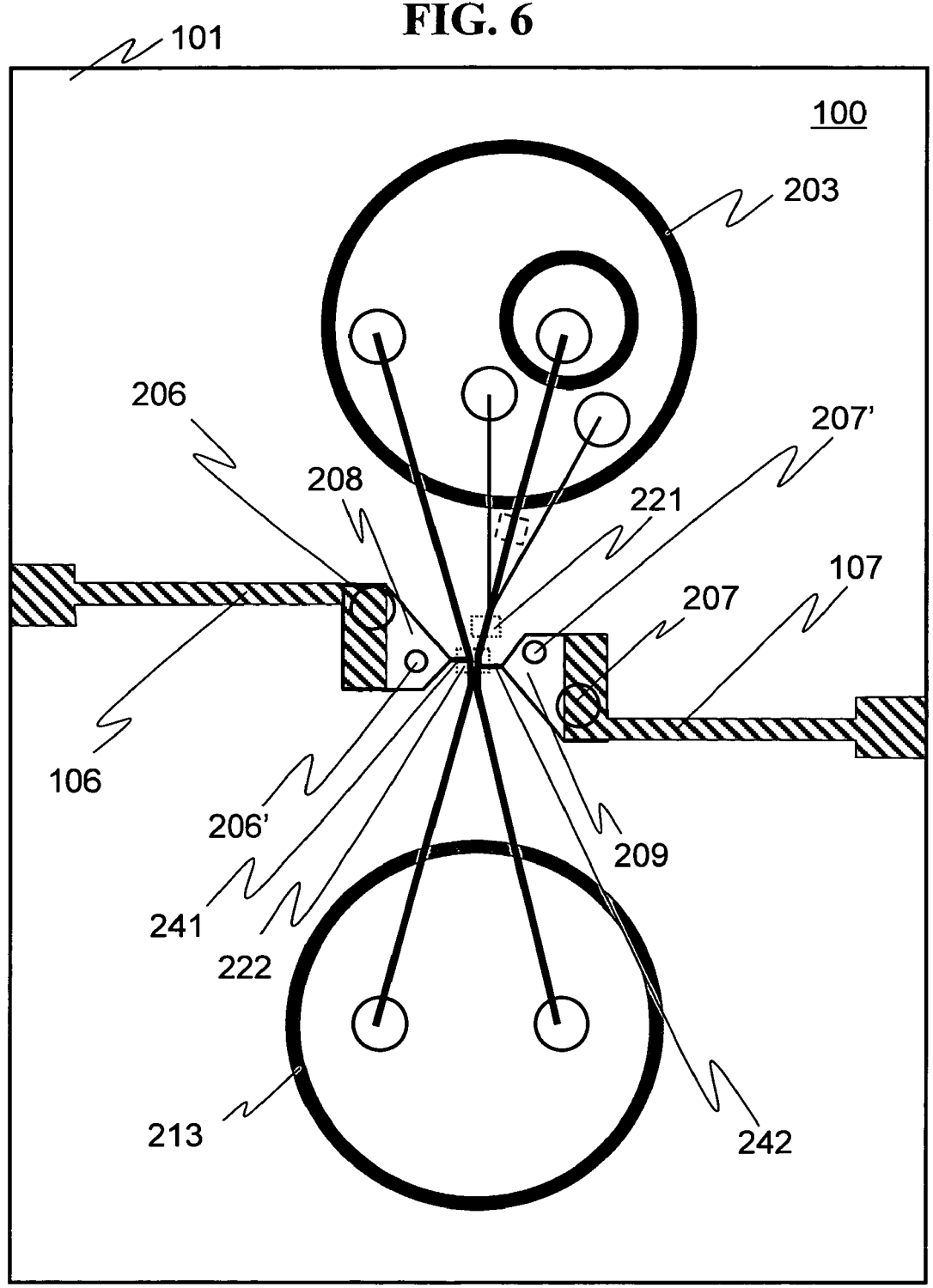
FIG. 6 is a plan view of a sell sorter chip with the gel electrode portions having a different structure.

FIG. 6 is a plan view illustrating a cell sorter chip in which the gel electrode section has a different structure. In this case, the wiring 106 and 107 in FIG. 1 and the electrodes inserted into the holes for introducing gel containing electrolytes are realized by a conductive film deposited on the laminate film 410 adhered on the bottom surface of the substrate 101. The laminate film 410 is adhered on the bottom surface of the substrate 101, and therefore the electrodes and other sections formed on the conductive film are depicted in FIG. 6 in the overlaid state to facilitate understanding of the relation with other components, although the components are now shown in the plan view of the chip.

The structure shown in FIG. 6 employs pentagonal microstructures 208, 209 in place of the microstructures 208, 209 shown in FIG. 1. The openings 206, 207 provided on the substrate 101 communicate with the pentagonal microstructures 208, 209, respectively, and the gel is injected through the openings. Reference numerals 206', 207' denote holes for air ventilation communicating with the microstructures 208, 209, respectively. During gel injection, when the gel overflows from the air ventilation openings 206', 207', the gel injection should be terminated. Coupling sections 241, 242 are provided on the protruding sections of the pentagonal microstructures 208, 209, respectively, so that the buffer fluid flowing down the flow path 247 may contact the gel. To achieve sufficient electric connection between the gel injected to the pentagonal microstructures 208, 209 and the deposited conductive films 106, 107 used in place of the wiring 106, 107, respectively, the conductive films 106, 107 are deposited at the respective position where the gel injected into the microstructures 208, 209 contact edge sections of the conductive films 106 and 107, respectively, with a proper area. Other edge sections of the conductive films 106 and 107 are formed with respective terminals to be connected to the power source 215.

The laminate film 410 is adhered to the substrate 101, so that the terminals at the other edge sections of the laminate film 106 and 107 are hidden by the substrate 101. Although not shown, a structure is provided which is connected to the terminals to establish connection with the power supply 215 on a surface of the substrate 101.

(Third Embodiment)

An algorithm for recognizing and sorting cells by means of image recognition using the cell sorter chip 100 shown in FIG. 1 is described below. As described with reference to FIG. 1, the cell suspension is injected into the hole 201. A wall 250 for preventing diffusion of the cell suspension is provided around the hole 201. The wall 250 is prepared in the reservoir 203, and a liquid surface in the hole 201 is equal to that in the reservoir 203. The cells flow from the hole 201 to the flow path 204, and join together with the flow path 205 constituting a side flow at a position just ahead the cell detecting area 221. Because of the join, the state where the cells are concentrated toward a central portion of the flow path can be realized. Refer to FIG. 3.

Images of the cells passing over the cell detecting area 221 in the flow path 204 are picked up with a CCD camera. A CCD camera capable of picking up 200 frames per second can be used for this purpose. With this image pick-up capability, even when a flow velocity of the buffer fluid flowing down the flow paths in the cell detecting area 221 is around 1 mm/sec, each of the cells can be recognized.

Figure 7:
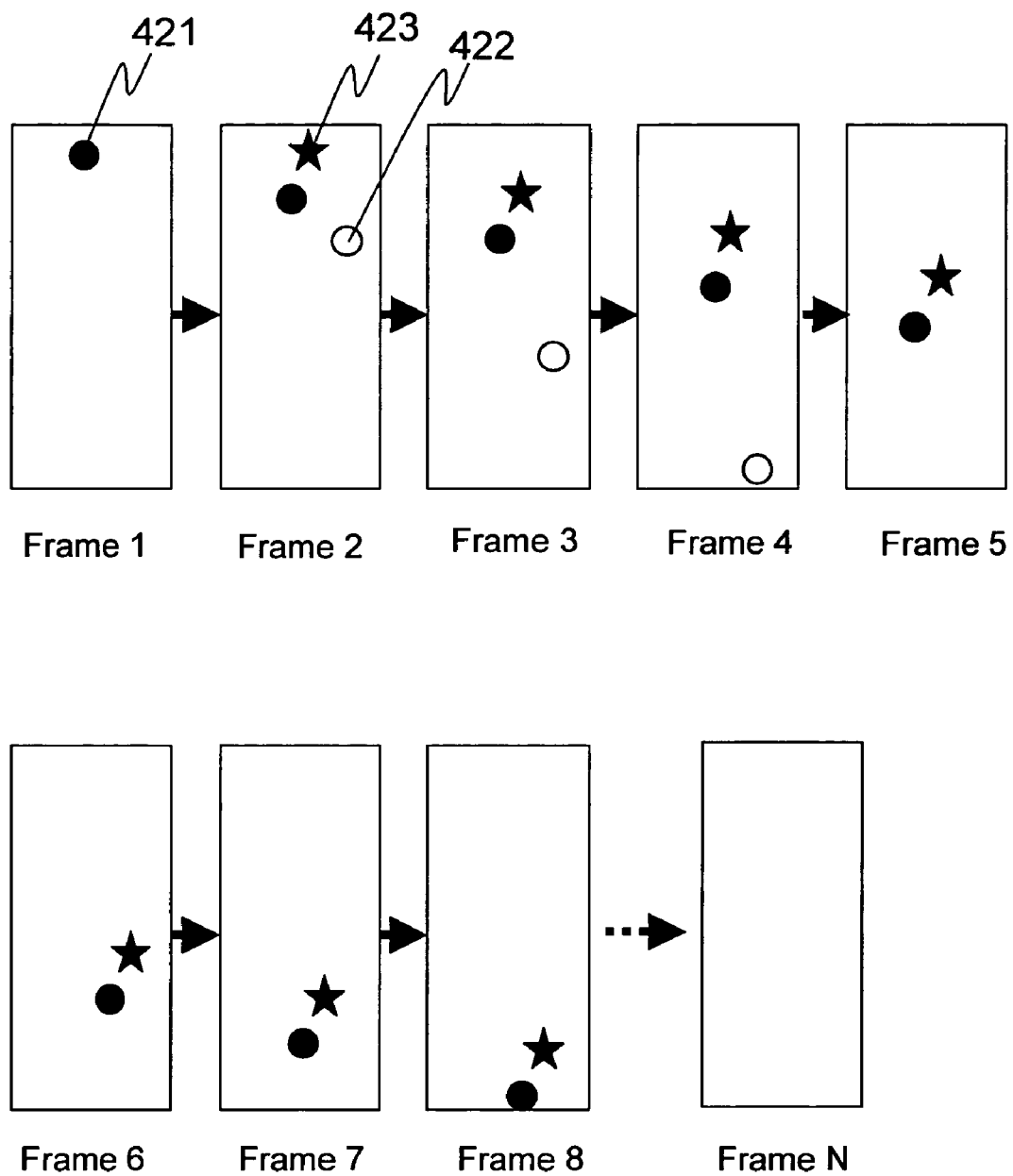
FIG. 7 is a diagram illustrating an algorithm for recognizing cells from images picked up with a CCD camera and numbering the cells.

FIG. 7 is a diagram for illustrating an algorithm for recognizing cells from the images picked up by the CCD camera, numbering and identifying each of the cells. In FIG. 7, the images successively picked up are numbered as frame 1, frame 2, . . . N, and the numbers denote cells appearing on the respective frames. On the frame 1, only a cell shown as a black circle appears. An image of the cell shown as the black circle is picked up, and is also numbered as No. 421. On the next frame 2, a cell shown as a white circle and a cell shown as a star appear in addition to the cell 421. The cells shown as a white circle and that shown as a star appear first on the frame 2 at the same time. Images of the cells are picked up, and smaller numbers are assigned to cells detected first on the downstream side. In this case, since the cell shown as a white circle appear on the downstream side of the cell shown as a star, the cell shown as a white circle is numbered as No. 422, and the cell shown as a star as No. 423. No new cell is recognized on the next frame 3. When the frame 2 is compared to the frame 3, it is understood that the cell of No. 422 migrates faster than the cells 421 and 423. Also on the next frame 4, no new cell is recognized. The cell 422 migrates fast, so that the cell appears on an edge of the image and can not clearly be recognized. On the other hand, the cells 421 and 432 migrate at the substantially same velocity. Up to frame 8 can be recognized. The cells on each frame are recognized by checking the illuminance barycenter, an area, a circumferential length, a major axis, and a minor acid as the indexes of each cell.

As described above, time required for each cell to migrate to the cell sorting region 222 (strictly, the coupling sections 241, 242) is computed from the migration velocity of the image-picked up and numbered cells, and the cells are sorted to the recovery hole 211 or recovery hole 212 by loading or by not loading a plus electric field to the gel electrode in the coupling section 242 or a minus electric field to the gel electrode in the coupling section 242. More specifically, a migration velocity (V) of the cells numbered from the image acquired once for every predetermined period of time is computed, and the cells are sorted according to the loading timing from the (L/V) to (L/V+T) wherein L is a distance previously inputted and T is a loading time.

(Fourth Embodiment)

In the fourth embodiment, examples of a preprocessing section for successively peeling off organ tissue from the surface and largely dividing the cell to cell layers, chip-shaped device with a cell sorting region integrated therein, and cell sorting to be performed by using the device are described. In the case described below, a colon polyp taken with an endoscope (with a diameter of about 3 mm) is used as a sample, and cells larger than the average cell are sorted by cell sorting.

Figure 8:
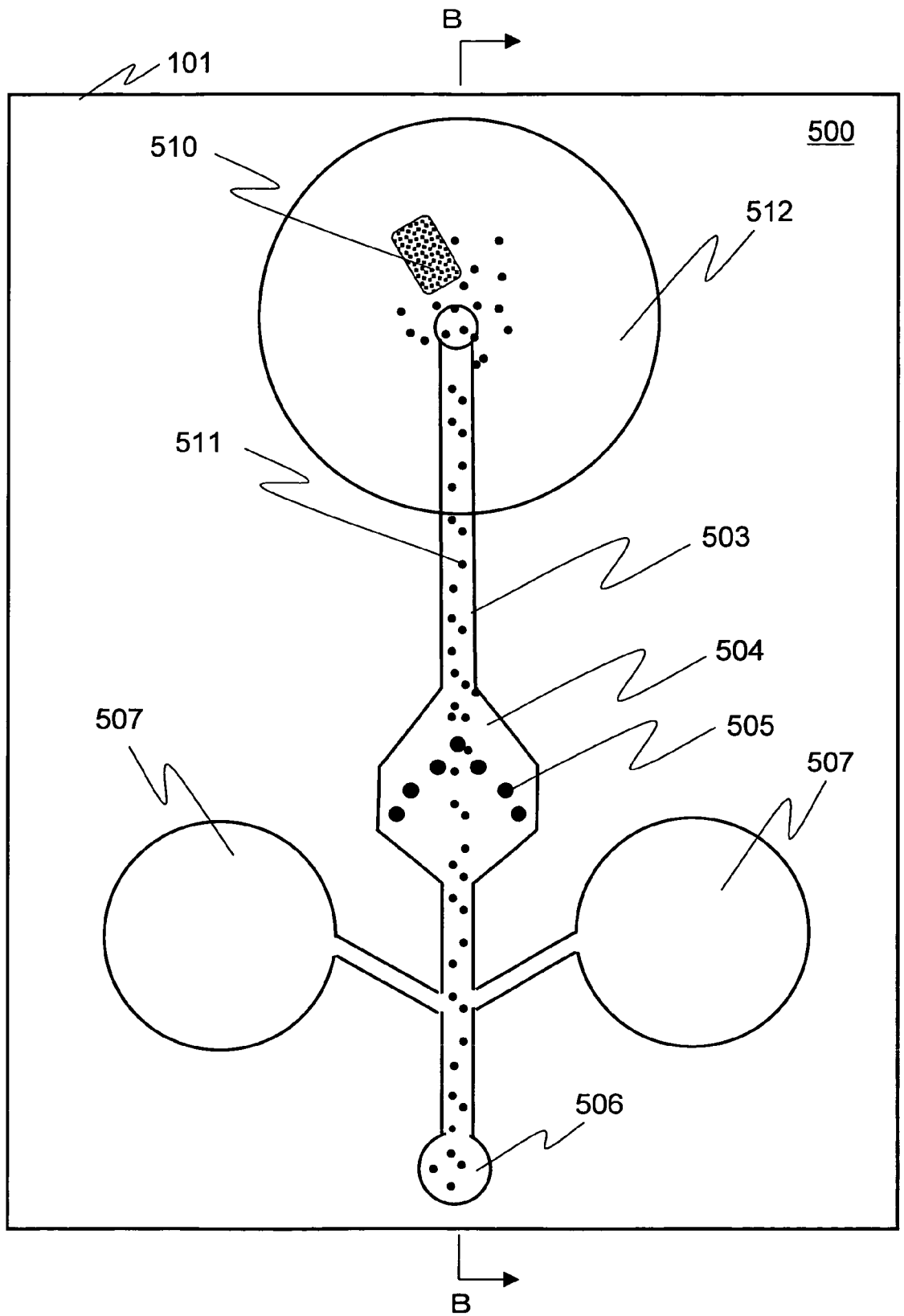
FIG. 8 is a plan view of a chip according to a fourth embodiment of the present invention.
Figure 9:
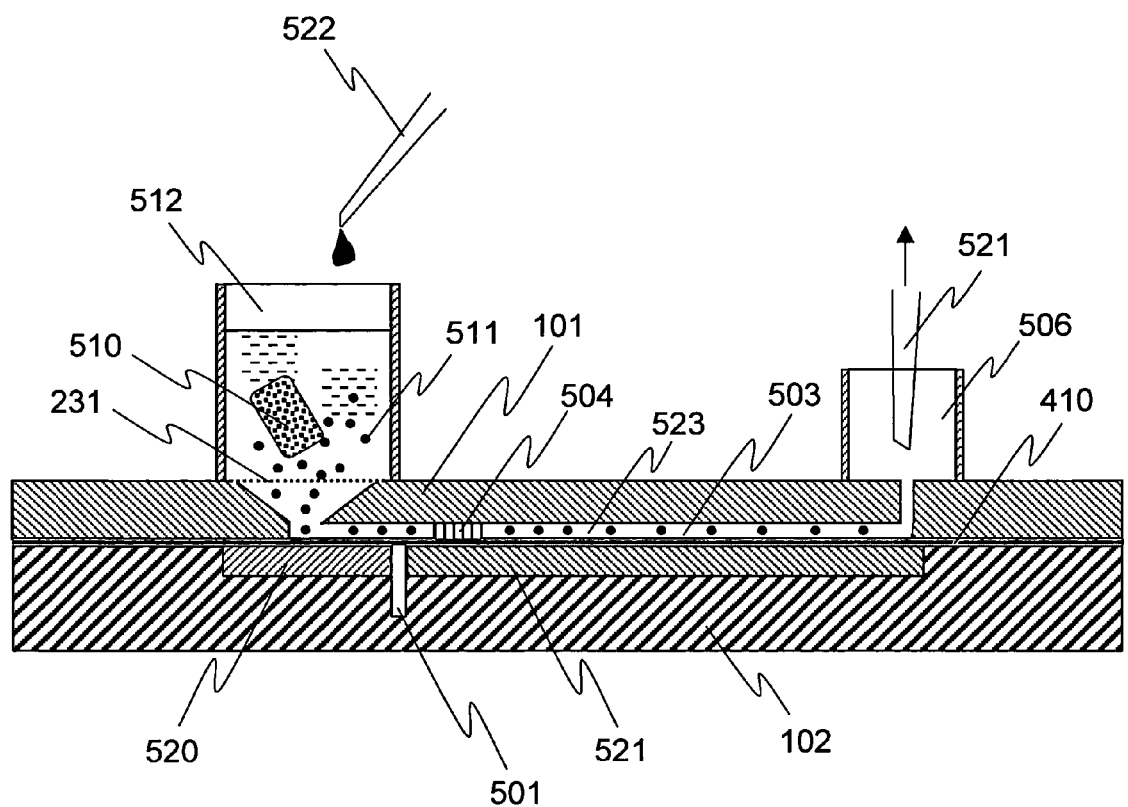
FIG. 9 is a cross-sectional view taken along the line B-B in FIG. 8 and viewed in the direction indicated by the arrowheads.

FIG. 8 is a plan view illustrating a chip according to the fourth embodiment, while FIG. 9 is a cross-sectional view taken along the line B-B in FIG. 8 and viewed in the line indicated by the arrow. Reference numeral 101 denotes a substrate, and a flow path 503 is formed on a bottom surface of the substrate. The reservoir 512 and reservoir 506 provided on a surface of the substrate through the openings are communicated with each other through corresponding openings at both ends thereof. The flow path 503 is formed as a groove engraved on a bottom surface of the substrate. As described with reference to FIG. 4 and FIG. 5, the laminate film 410 is attached on the flow path 503. The reservoirs 512, 506 provided at two ends of the flow path 503 are formed in such a manner that they are attached on the substrate surface after the corresponding openings have been formed, and the laminate film 410 is adhered thereon to form the flow path 503. A filter 504 is provided on the way of the flow path 503. The filter 504 has a number of pillars 505 arrayed side by side.

The substrate 101 is placed over a substrate 102 with a temperature controller 520 provided at a position opposite to a lower surface of the reservoir 512 and a temperature controller 52 provided at a position opposite to a lower surface of the flow path 503 with the bottom surface of the substrate facing downward. The temperature controllers 520, 521 keep the reservoir 512 and the flow path 503 at different temperatures, respectively. A slit 501 is provided for thermal insulation between the temperature controllers 520, 521. The slit may be a simple cut for forming an air layer, or may be made with a heat-insulating material.

Prior to start of use thereon, a prespecified quantity of buffer fluid is injected in the reservoir 512 to fill the flow path 503 with the buffer fluid. Furthermore, a buffer fluid containing a trypsin inhibitor for inhibiting the trypsin activity is injected in the reservoir 507. A tissue piece 510 as a sample is placed in the reservoir 512, and a solution including a prespecified quantity of trypsin is added in the buffer fluid reservoir 512 with a pipette 522. A cell matrix on tissue surface is decomposed by trypsin, and the cells 511 are successively peeled off from the surface of the tissue piece 510. The temperature controller 520 keeps the reservoir 512 at a prespecified temperature so that the processing is performed efficiently. The cells 511 peeled off from a surface of the tissue piece 510 are guided to the flow path 503 in association with migration of the buffer fluid due to a different between liquid levels in the reservoirs 512 and 506. Cells blocks or other structures not sufficiently dispersed are removed with the filter 504 provided in the flow path 503 and the dispersed cells are guided to the reservoir 506. The temperature controller 521 keeps the flow path 503 at a prespecified temperature for preventing excessive decomposition of the cells by trypsin when the cell 511 migrates in the flow path 503.

A low path communicated to the reservoir 507 is connected to a flow path connecting the filter 504 to the reservoir 506, and the buffer fluid containing the trypsin inhibitor is filled in the reservoir 507. Therefore, the trypsin inhibitor acts to the cell 511 having passed through the filter 504. Therefore, the cell 511 reaches the reservoir 506 in the stable state where the cells are not affected by trypsin. The cells 511 having reached the reservoir 506 can successively be recovered with the pipette 521. From the cells recovered as described above, giant cells are sorted with the cell sorter chip 100 described in the first embodiment and shown in FIG. 1. In some samples, 80% of the giant cells which can be sorted as described above have been turned into cancer cells. A single reservoir 507 may be used.

It may be said that the chip 500 described with reference to FIG. 8 and FIG. 9 has a role as a sorter for successively sorting the dispersed cells sequentially peeled off from the tissue piece as a sample. The chip 500 can be regarded as a preprocessing chip for obtaining sample cells for the cell sorter chip 100 described in the first embodiment with reference to FIG. 1.

Figure 10:
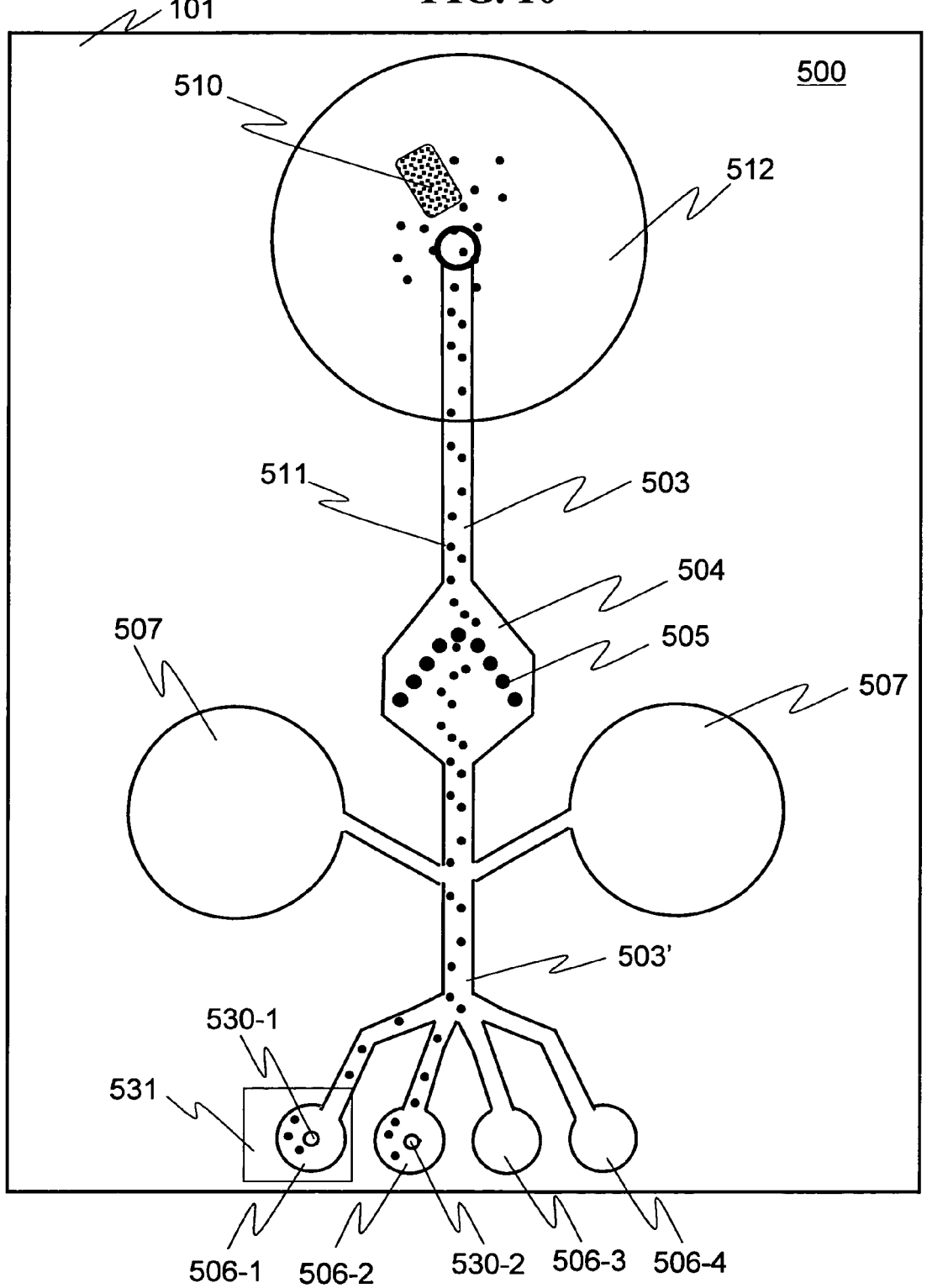
FIG. 10 is a plan view illustrating an example of a chip configured to be used as a preprocessing chip for obtaining sample cells for a cell sorter chip.

FIG. 10 is a plan view showing an example of a chip especially used as a preprocessing chip for obtaining the sample cells for the cell sorter chip. As clearly understood from comparison to FIG. 8, the cells are digested by trypsin from the sample tissue piece in the reservoir 512, and the dispersed cells flow from the tissue surface into the flow path 503 and flow down through the filter 504, where the buffer fluid containing the trypsin inhibitor is supplied from the reservoir 507 as described with reference to FIG. 8.

In the chip shown in FIG. 10, the flow path 503 branches at an utmost down stream section 503'. Furthermore, ends of the branched flow paths are communicated to respective sealed reservoirs 506-1 to 506-4. As clearly understood by referring to FIG. 9, a top face of the reservoir 506 is open. In contrast, a closed reservoir is covered with a seal on the top surface thereof, so that any liquid can not flow into the closed reservoir. When a hole is provided on a seal covering the top face of the reservoir with a pin, the liquid flows only into the reservoir with a hole opened thereon. Therefore, after the buffer fluid containing cells are recovered for a prespecified period of time into a reservoir, and the hole is covered with an adhesive tape, and then a hole is provided on a seal for the next reservoir to recover the buffer fluid contained therein. By repeating the operations as described above, cells time-sequentially sorted can be recovered. If all reservoir are closed with seals at the first point of time, it is impossible to inject a buffer fluid into a flow path for filling the flow path with the buffer fluid. Therefore, it is necessary to keep open at least one reservoir.

FIG. 10 illustrates the state where a hole 530-1 is provided on an upper surface seal for the reservoir 506-1 to recover the buffer fluid containing cells from the hole, with the hole closed with the adhesive tape 531 and then a hole 530-2 is provided on an upper surface seal for the reservoir 506-2 to recover the buffer fluid containing cells. The cells remaining in the branched flow paths when the hole on the upper seal is closed remain as they are in the branched flow paths.

(Fifth Embodiment)

The fifth embodiment relates to a cell sorter capable of sequentially sorting a cell from a piece of tissue by making use of a chip with the pretreatment chip according to the fourth embodiment and the cell sorter chip according to the first embodiment integrated therewith to trypsin-treat the piece of tissue, as well as capable of collecting a specific cell group only among the sequentially dispersed cells.

Figure 11:
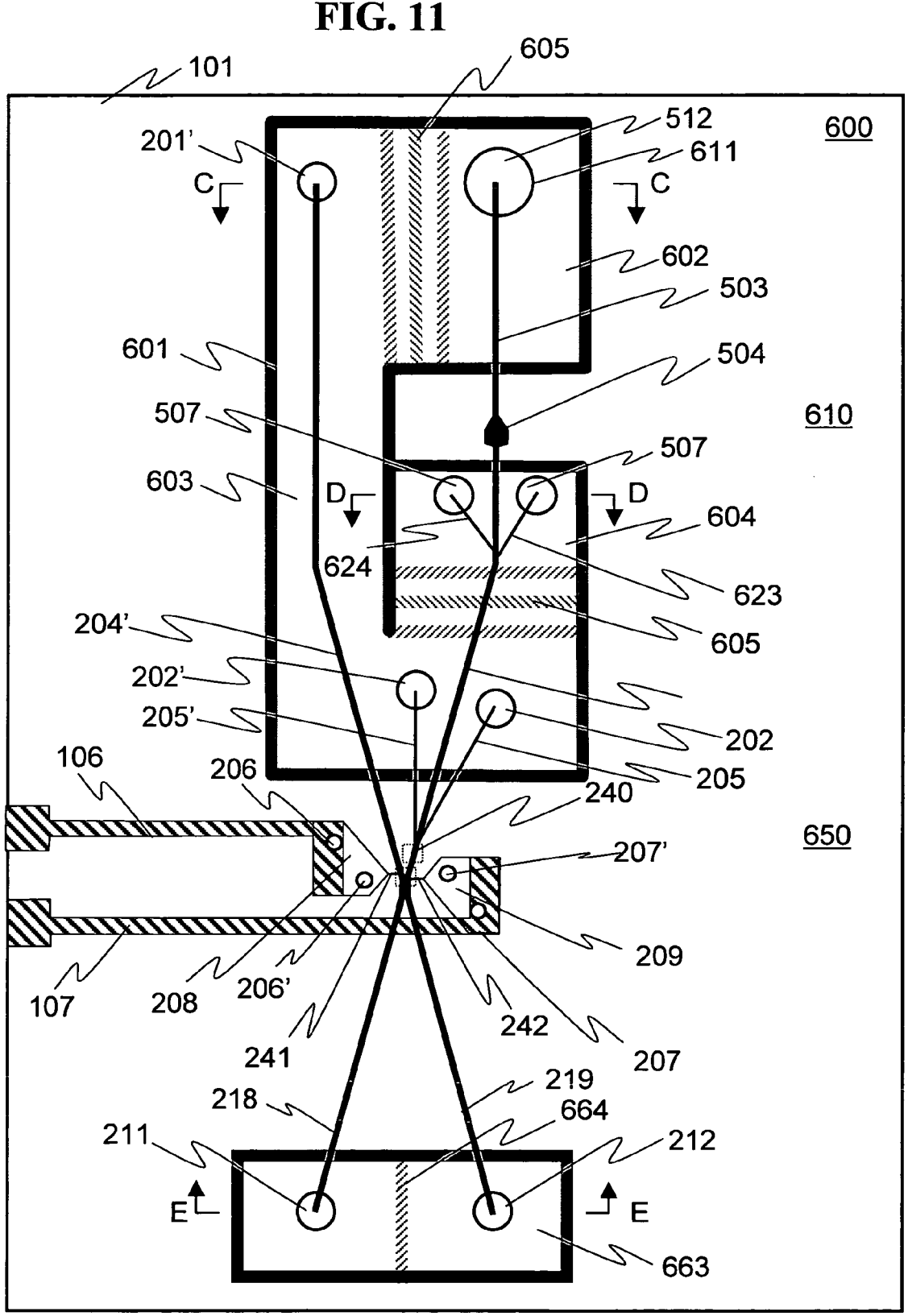
FIG. 11 is a schematic plan view of a cell sorter according to a fifth embodiment of the present invention.
Figure 12:
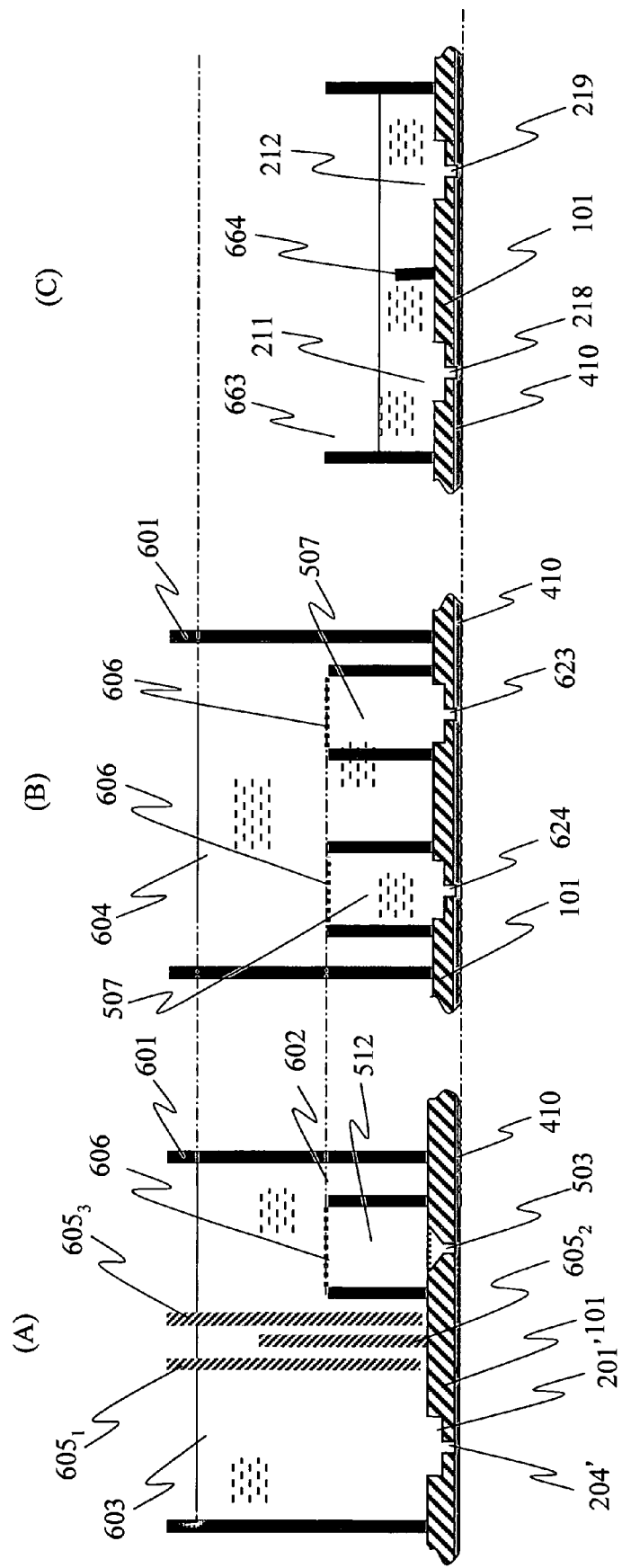
FIGS. 12(A), 12(B) and 12(C) are cross-sectional views illustrating the cell sorter according to the fifth embodiment taken along lines C-C, D-C, and E-E, respectively and viewed in the direction indicated by the arrowheads.

FIG. 11 is a plan view schematically illustrating a cell sorter according to the fifth embodiment. FIG. 12(A), FIG. 12(B) and FIG. 12(C) are cross-sectional views illustrating the cell sorter in FIG. 11 taken along the lines C-C, D-C, and E-E respectively and viewed in the direction indicated by the arrow. In FIG. 11 and FIG. 12, the same reference numerals are assigned to the same components or those having the substantially same functions as explained in the embodiments already described.

Reference numeral 600 indicates a cell sorter in the fifth embodiment. A trypsin treating section 610 and a cell sorting section 650 are set up on a substrate 101 and are connected in cascade. A reservoir 601 is partitioned into three chambers 602, 603, 604. Configuration of a partition 605 between the chambers is shown in FIG. 12(A). Herein the configuration of a partition between the chambers 602 and 603 is described as an example. The partition 605 between the chamber 602 and chamber 603 includes partition plates $605_1$, $605_2$, $605_3$. The partition plates $605_1$, $605_2$, $605_3$ are placed with a distance of 100 μm between in this embodiment, and the partition plates $605_1$ and $605_3$ each have a gap of 100 μm therebetween and the bottom face of the chamber 603. The chambers 602 and 603 are in communication with each other through a space 100 μm in width. The partition 605 between the chambers 603 and 604 has the same configuration as described above. A buffer fluid is put into the whole of the three chambers. In this step, it is important for a solution level of the buffer fluid to be in a higher position than the top surface of the partition plate $605_2$ and in a lower position than the top surface of the partition plates $605_1$ and $605_3$. The solution level is 12 to 15 mm in height.

The chamber 602 includes a reservoir 512, which is the same as the reservoir 512 described in FIG. 8. However, it is assumed herein that the solution level is in a lower position than that of the buffer fluid filled in the chamber 602, for instance, 10 mm in height. A piece of tissue and a trypsin solution are put in the reservoir 512 with the volume half of the reservoir 512. The trypsin solution is adjusted to have the specific gravity of 1.04 using glycerin. When the tissue would not sink in the trypsin solution, the tissue is adjusted to have the same specific gravity as the buffer fluid, and a filter about 10 μm in thickness is placed on the top surface of the wall 611. This operation prevents a cell or trypsin present in the reservoir 512 from leaking into the chamber 602. Trypsin yet leaking into the chamber 602 is needed to be prevented from passing further to the chamber 603. The partition plate 605 is provided for this purpose.

In use, the cell sorter 600 is placed on a substrate with the same temperature controllers 520, 521 same as those described in FIG. 9 provided thereon. But the substrate with the temperature controllers 520, 521 provided thereon is omitted in the figure. An opening in communication with a flow path 503 is on the bottom surface of the reservoir 512, and is connected to the filter 504 as described in FIG. 8. Flow paths 623, 624 in communication with the reservoir 507 converge downstream of the filter 504, and a buffer fluid put in the reservoir 507 and containing a trypsin inhibitor is supplied as described in FIG. 8. Therefore the trypsin inhibitor acts on cells passing through the filter 504, and the cells become free from the influence of trypsin. The reservoir 507 herein is provided in the chamber 604 partitioned with the chamber 603 and the partition plate 605 as in the case of the chamber 602. FIG. 12(B) is a cross-sectional view illustrating a portion of the chamber 604 and the reservoir 507. Since the chamber 604 is partitioned with the partition plate 615, the height of a solution level of the buffer fluid is the same as that of the chamber 602 as shown in the description of the chamber 602. Further, the reservoir 507 is configured to have the same height as that of the reservoir 512, which contains a buffer fluid having the same specific gravity as that in the reservoir 512. Therefore a buffer fluid containing the trypsin inhibitor converges with another buffer fluid containing cells flowing down in a flow path 503, downstream of the filter 504, and releases the cells from the influence of trypsin. The converged buffer fluid flows down in a flow path 204. The temperature controllers 521 is provided on the under surface of the reservoir 507 as described in FIG. 9. Further, a filter 606 is provided on the top surface of the reservoir 512 like in the reservoir 512, if necessary.

The chamber 602 and the chamber 604 constitutes the trypsin treating section 610 for trypsin-treating a piece of tissue and sequentially sorting a cell from the piece of tissue, and functions as a cell supplier to the cell sorting section 650.

On the other hand, a hole 201' is provided in the chamber 603 as shown in FIG. 12(A), and a flow path 204' in communication with the hole 201' is opened. Holes 202, 202' are further opened downstream of the chamber 604 in the chamber 603, and a flow path 205 and a flow path 205' are in communication with the holes 202, 202'. A buffer fluid is supplied to the flow paths through the holes described above. The system constituted for a buffer fluid containing cells supplied from the flow path 204 and a buffer fluid supplied from the flow paths 204', 205, 205' is the same as that for the cell sorter described in FIG. 6, and constitutes the cell sorting section 650.

A buffer fluid containing cells obtained in flow paths 218, 219 is collected in reservoirs 211, 212, and FIG. 12(C) shows a cross-sectional view of a reservoir 663 including the reservoirs 211, 212 taken along the line E-E and viewed in the direction indicated by the arrow. The solution level of a buffer in the reservoir 663 is made to be lower than those in the chambers 602 through 604, which is used as energy for the buffer to flow down in the flow path.

As shown in FIGS. 12(A) to 12(C), the under surface of the substrate 101 is coated with a laminate film 410, the surface making a groove cut on the substrate 101 closed off as a flow path. As described in FIG. 6, an electrode inserted in a hole for introducing wiring 106, 107 and gel containing electrolyte can be implemented by means of a conductive membrane deposited on a laminate film. In this case, since the laminate film 410 is attached to the under surface of the substrate 101 as described in FIG. 6, an electrode provided on a conductive membrane is not actually visible on the plan view of the chip. However, it is stuck for the purpose of an easier understanding of the relation thereof with other components. Further, a configuration is provided in which an end section defining a terminal to be connected to a power source 215 for the conductive membranes 106, 107 can be connected to the power source 215 on the surface of the substrate 101.

(Sixth Embodiment)

Figure 13:
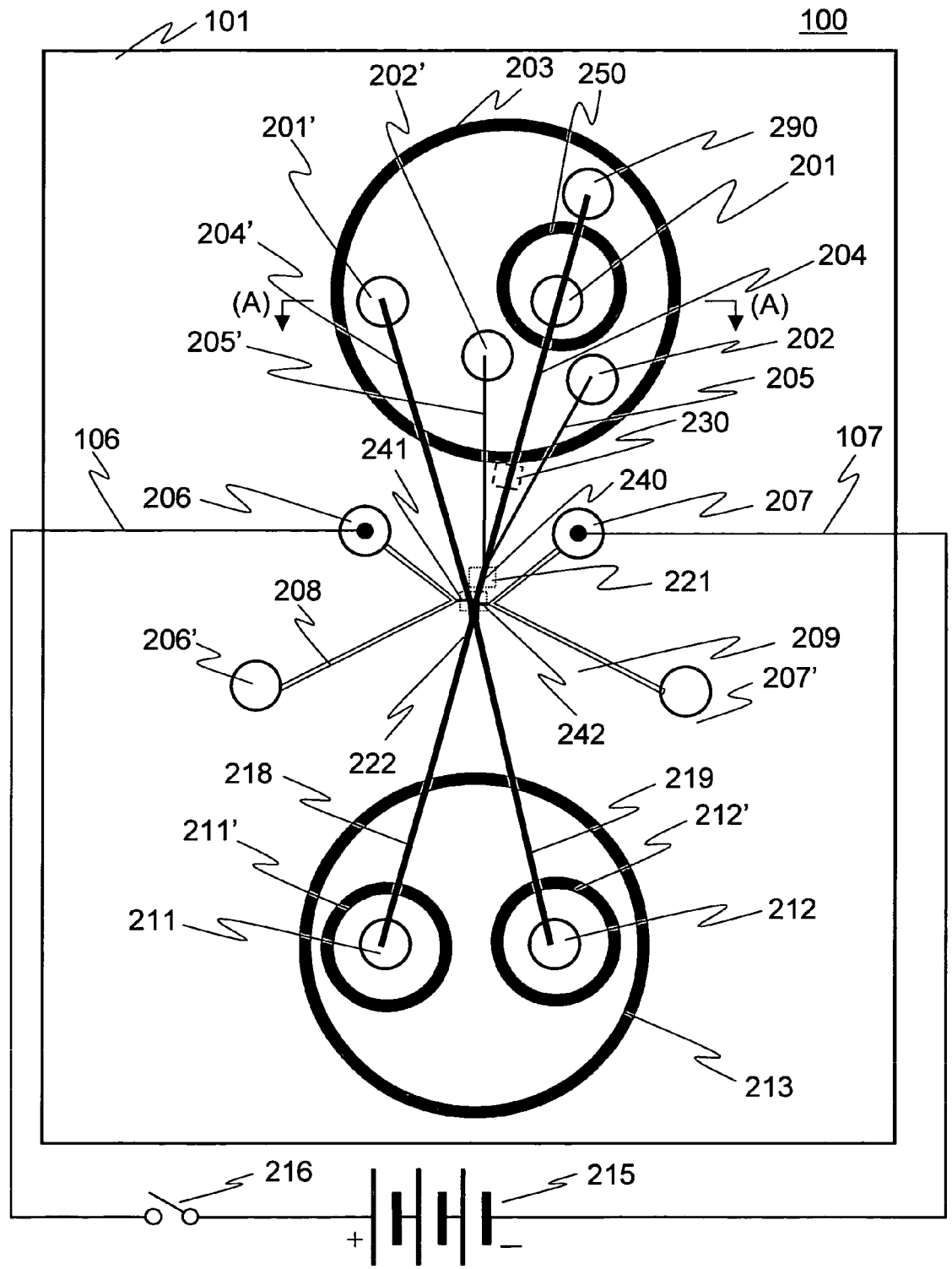
FIG. 13 is a plan view schematically illustrating an example of system configuration of a cell sorter according to a sixth embodiment of the present invention.
Figure 14:
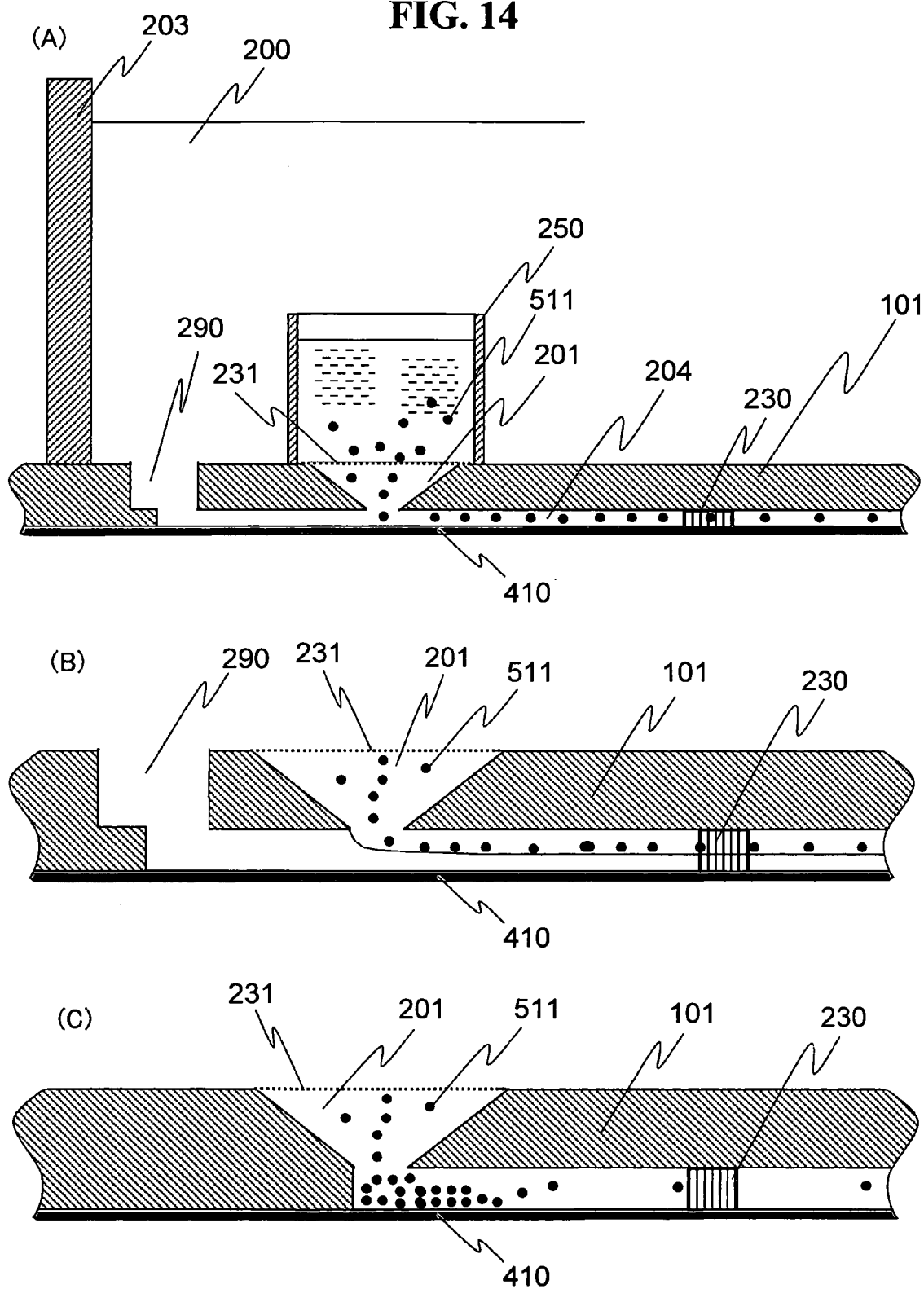
FIGS. 14(A), 14(B) and 14(C) are partial cross-sectional views for explaining a devise in a sample cell inlet portion according to the sixth embodiment.

The sixth embodiment is contrived for inletting a sample cell in the first embodiment. FIG. 13 is a plan view schematically illustrating an example of system configuration of the cell sorter according to the sixth embodiment. FIGS. 14(A), 14(B) and 14(C) are partial cross-sectional views for explaining a devise in a sample cell inlet portion according to the sixth embodiment. The same reference numerals as in the first embodiment are assigned to the same components or those having the substantially same functions herein.

As clearly shown when FIG. 13 is compared to FIG. 1, the cell sorter in the sixth embodiment is the same as that in the first embodiment, except that the flow path 204 in the first embodiment is extended to further upstream, and an opening 290 is provided to inlet a buffer fluid. As seen in FIG. 14(A), the flow path 204 is in communication with a reservoir 250 through an opening 201, and is also extended to further upstream to be in communication with the opening 290.

FIG. 14(B) schematically shows a buffer fluid and cells flowing from the opening 201 and the opening 290 to the flow path 204, and, according to the sixth embodiment, a layer of the buffer fluid flowing from the opening 290 to the flow path 204 prevents the buffer fluid and cells flowing from the opening 201 to the flow path 204 from contacting a laminate film 410. Namely, the buffer fluid and cells flowing from the opening 201 to the flow path 204 flow on the layer of the buffer fluid flowing from the opening 290 to the flow path 204. This can therefore prevent the cells from contacting the laminate film 410 and from stagnation resulting from the contact.

FIG. 14(C) schematically shows how the cells flowing from the opening 201 to the flow path 204 contact the laminate film 410, and stagnation takes place resulting from the contact. If one of the cells contacts the laminate film 410 and thus stagnates thereon, another cell gets stuck on the cell, which results in stagnation of other cells one after another, and eventually the flow of the cells is brought to a standstill.

Descriptions of the sixth embodiment are provided taking an example in which the flow path 204 in the first embodiment is extended to further upstream, and it is obvious that the same configuration is allowable to the flow path 503 in the fourth and fifth embodiments. Namely, a buffer fluid is inlet on the upstream side compared to the position in which the cells are inlet to form a flowing layer of the buffer fluid, and then the cells are inlet, thereby preventing the cells from contacting the bottom face of the flow path.

With the present invention, a disposable type of cell sorter chip capable of stably sorting cells can be realized.

What is claimed is:

1. A chip for cell sorting comprising:
   a substrate; and, provided on the substrate, the following:
   a first flow path which allows a sample fluid containing cells to flow down;
   second and third flow paths which are provided on both respective sides of said first flow path and which allow a buffer fluid not containing cells to flow down;
   a first reservoir for supplying the sample fluid containing the cells to the first flow path;

a second reservoir for supplying the buffer fluid to the second and the third flow paths;

a fourth flow path which allows a fluid to flow down, said fluid being formed by confluence of the sample fluid from the first flow path and the buffer fluid from the second and third paths;

a cell detecting region provided on the fourth flow path for detecting cells flowing with the fluid flowing down the fourth flow path;

a cell sorting region provided downstream of the cell detecting region of the fourth flow path for sorting the cells according to the type of the cells detected;

at least two flow paths downstream of said cell sorting region, said flow paths allowing sorted cells to flow down, and wherein the first reservoir is formed with a boundary wall for holding the sample fluid containing the cells, said boundary wall being formed inside of the second reservoir.

2. The chip for cell sorting according to claim 1 wherein said second reservoir, said second flow path and said third flow path are configured so that the buffer fluid not containing cells flows in the second and third flow paths at substantially the same pressure.

3. A chip for cell sorting according to claim 1, further comprising:
a fifth flow path which is provided upstream of said first flow path and allows a buffer fluid not containing cells to flow down.

4. A method for sorting cells using a chip for cell sorting which comprises:
a substrate; and, provided on the substrate, the following:
a first flow path which allows a sample fluid containing cells to flow down;
second and third flow paths which are provided on both respective sides of said first flow path and which allow a buffer fluid not containing cells to flow down, said method comprising:
supplying the sample fluid containing the cells from a first reservoir to the first flow path;
supplying the buffer fluid from a second reservoir to the second and the third flow paths;
providing a fourth flow path which allows a fluid to flow down, said fluid being formed by confluence of the sample fluid from the first flow path and the buffer fluid from the second and third paths;

detecting cells flowing with the fluid flowing down the fourth flow path via a cell detecting region;

sorting the cells according to the type of the cells detected via a cell sorting region provided downstream of the cell detecting region of the fourth flow path; and allowing sorted cells to flow down at least two flow paths downstream of said cell sorting region, wherein the first reservoir is formed with a boundary wall for holding the sample fluid containing the cells, said boundary wall being formed inside of the second reservoir.

5. A chip for flow cytometry comprising:
a substrate; and, provided on the substrate, the following:
a first flow path which allows a sample fluid containing cells to flow down;
second and third flow paths which are provided on both respective sides of said first flow path and which allow a buffer fluid not containing cells to flow down;
a first reservoir for supplying the sample fluid containing the cells to the first flow path;
a second reservoir for supplying the buffer fluid to the second and the third flow paths;
a fourth flow path which allows a fluid to flow down, said fluid being formed by confluence of the sample fluid from the first flow path and the buffer fluid from the second and third paths;
a cell detecting region provided on the fourth flow path for detecting cells flowing with the fluid flowing down the fourth flow path;
a drain provided downstream of the cell detecting region; and
wherein the first reservoir is formed with a boundary wall for holding the sample fluid containing the cells, said boundary wall being formed inside of the second reservoir.

6. The chip for flow cytometry according to claim 5 wherein said second reservoir, said second flow path and said third flow path are configured so that the buffer fluid not containing cells flows in the second and third flow paths at substantially the same pressure.

7. A chip for flow cytometry according to claim 5, further comprising:
a fifth flow path which is provided upstream of said first flow path and allows a buffer fluid not containing cells to flow down.

* * * * *